(12) United States Patent
Rambaran et al.

(10) Patent No.: US 10,953,042 B2
(45) Date of Patent: Mar. 23, 2021

(54) VANADIUM INSULIN-MIMETICS, METHODS OF PREPARATION, AND METHODS FOR TREATMENT OF DIABETES

(71) Applicant: The University of Trinidad and Tobago, Arima (TT)

(72) Inventors: Varma Rambaran, St. Augustine (TT); Saumya S. Mani, Alleppy (IN)

(73) Assignee: The University of Trinidad and Tobago, Arima (TT)

( * ) Notice: Subject to any disclaimer, the term of this patent is extended or adjusted under 35 U.S.C. 154(b) by 0 days.

(21) Appl. No.: 16/699,676

(22) Filed: Dec. 1, 2019

(65) Prior Publication Data

US 2020/0138857 A1    May 7, 2020

Related U.S. Application Data

(63) Continuation of application No. PCT/TT2018/000001, filed on Jun. 1, 2018.

(60) Provisional application No. 62/514,254, filed on Jun. 2, 2017.

(51) Int. Cl.
*A61K 33/24* (2019.01)
*C07F 9/00* (2006.01)
*A61K 9/00* (2006.01)
*A61K 9/16* (2006.01)
*A61P 3/10* (2006.01)

(52) U.S. Cl.
CPC ............ *A61K 33/24* (2013.01); *A61K 9/0053* (2013.01); *A61K 9/1611* (2013.01); *A61K 9/1652* (2013.01); *A61P 3/10* (2018.01); *C07F 9/005* (2013.01)

(58) Field of Classification Search
CPC .................................................... A61K 33/24
See application file for complete search history.

(56) References Cited

U.S. PATENT DOCUMENTS 8,685,538 B2 * 4/2014 Torchilin ............. A61K 9/5138
428/403

OTHER PUBLICATIONS

Hermansen et al. (Vasc. Health and Risk Mgmt., 2008, 4(3), 561-574) (Year: 2008).*
Bhunia et al. (Langmuir, 2011, 27(24), 15322-15329) (Year: 2011).*
Vallet-Regi et al. (Chem. Mater., 2001, 308-311).*
Baran, Enrique J., Model Studies Related to Vanadium Biochemistry: Recent Advances and Perspectives, J. Braz. Chem. Soc., 2003,vol. 14, No. 6, 878-888.
Bertrand, N. et al., Transmembrane pH-Gradient Liposomes to Treat Cardiovascular Drug Intoxication, ACS Nano, 2010, vol. 4, No. 12, 7552-7558.
Domingo, Jose L, Vanadium and Tungsten Derivatives as Antidaibetic Agents, Biological Trace Element Research, 2002, vol. 88, 97-112.
Domingo, Jose L. et al., Toxicology of vanadium compounds in diabetic rates: The action of chealting agents on vanadium accumulation, Molecular and Cellular Biochemistry, 1995, 153: 233-240.
Hare, Ruth S., Endogenous Creatinine in Serum and Urine, Proc Soc Exp Biol Med, 1950, 74:148-151.
International Search Report dated Dec. 4, 2018.
Katada, Hitoshi et al., Crystal structure of Ce(IV)/dipicolinate complex as catalyst for DNA hydrolysis, J Biol Inorgc Chem, 2008, 13(2): 249-255.
Kim, H. et al., Glucose-Responsive Disassembly of Polymersomes of Sequence-Specific Boroxole-Containing Block Copolymers under Physiologically Relevant Conditions, ACS Macro Lett, 2012, 1:1194-1198.
Kumar, BVVS et al., Glucose- and pH-Responsive Charge-Reversal Surfaces, Langmuir, 2014, 30:4540-4544.
Lalwani, G. et al., Tungsten Disulfide Nanotubes Reinforced Biodegradable Polymers for Bone Tissue Engineering, Acta Biomater, 2013, 9(9):8365-8373.
Lalwani, G. et al., Two-Dimensional Nanostructure-Reinforced Biodegradable Polymeric Nanocompsites for Bone Tissue Engineering, Biomacromolecules, 2013, 14(3): 900-9.
Lee, Jung-Jae et al., Synthetic Ligand-Coated Magnetic Nanoparticles for Microfluidic Bacterial Separation from Blood, Nano Letters, 2014, 14(1):1-5.
Mura, Simona et al., Stimuli-responsive nanocarriers for drug delivery, Nat Mater, 2013, 12:991-1003.
Nayak, S. Sudhakar and Pattabiraman, TN, A new Colorimetric Method for the Estimation of Gylcosylated Hemoglobi, Clin Chim Acta, 1981, 109:267-274.
Peters, Kevin G. et al., Mechanism of insulin sensitization by BMOV (bis maltolato oxo vanadium); unliganded vanadium (VO4) as the active component, Journal of Inorganic Biochemistry, 2003, 96: 31-330.
Rao, Shasha et al., Perspective and potential of oral lipid-based delivery to optimize pharmacological therapies against cardiovascular diseases, J. Control Release, 2014, 193:174-187.
Reitman, Stanley & Frankel, Sam, A colorimetric Method for the Determination of Serum Glutamic Oxalacetic, and Glutamic Pyruvic Transaminases, Am J Clin Pathol, 1957, 28:56-63.
Selvi, B. Ruthrotha et al., Intrinsically Flourescent Carbon Nanospheres as a Nuclear Targeting Vector: Delivery of Membrane-Impermeable Molecule to Modulate Gene Expression In Vivo, Nano Letters, 2008, 8(10):3182-3188.
Selvi, Ruthrotha B et. al., ATP driven clathrin dependent entry of carbon nanospheres prefer cell with glucose receptors, Journal of Nanobiotechnology, 2012, 10:35.
Soni, Sanjeev et al., Role of optical coefficients and healthy tissue-sparing characteristics in gold nanorod-assisted thermal therapy, Int J Hyperthermia, 2013, 29(1):87-97.

(Continued)

*Primary Examiner* — Erin E Hirt
(74) *Attorney, Agent, or Firm* — Gorman IP Law

(57) ABSTRACT

Disclosed are vanadyl complexes of Formula 1, Formula 2, and Formula 3, wherein $R_1$, $R_2$, and R are defined as in the description. The pharmaceutical compositions containing these complexes and uses of the complexes for treatment of Diabetes Mellitus, such as Diabetes Mellitus Type 2, are also disclosed.

19 Claims, 15 Drawing Sheets

(56) References Cited

OTHER PUBLICATIONS

Sun, Xiaoming and Li, Yadong, Colloidal Carbon Spheres and Their Core/Shell Structures with Noble-Metal Nanoparticles, Angew Chem, 2004, 43(5):597-601).

Wang, Beilei et al., Glucose-Responsive Micelles from Self-Assembly of Poly(ethylene glycol)-b-Poly(acrylic acid-co-acrylamidophenylboronic acid) and the Controlled Release of Insulin, Langmuir, 2009, 25(21):12522-12528.

Wang, Daoyong et al., Aerobic C-H Acetoxylation of 8-Methylquinoline in Pd -Pyridinecarboxylic Acid Systems: Some Structure-Reactivity Relationships, Organometallics, 2013, 32:4882-489.

Willsky, G et al., Anti-diabetic effects of a series of vanadium dipicolinate complexes in rats with streptozotocin-induced diabetes, Coordination Chemistry Reviews 255, 2011, 2258-2269.

Written Opinion dated Dec. 4, 2018.

Zhao, Yannan et al., Mesoporous Silica Nanoparticle-Based Doube Drug Delivery System for Glucose-Responsive Controlled Release of Insulin and Cyclic AMP, J Am Chem Soc, 2009, 131(24): 8398-8400.

Seifter,S. et al., The estimation of gycogen with the anthrone reagent, Arch. Biochem., 1950, 25:abstract.

Bersted et al., "The Crystal and Molecular Structure of Orthorhombic Vanadyl(IV) Pyridine-2,6-dicarboxylate Tetrahydrate", vol. 7, No. 8, pp. 1557-1562, 1968.

Bombi et al., "Complexation of 2,6-pyridinedicarboxylic and 2,6-pyridinediacetic acids towards aluminium(III) and iron (III)", Polyhedron, vol. 28, pp. 327-335, 2009.

Boodram et al., "Investigations into an Intramolecular Proton Transfer and Solvent Dependent Acid-Base Equilibria in 2,6-Pyridine Diacetic Acid", ChemistrySelect, vol. 4, pp. 4301-4307, 2019.

Buglyo et al., "Aqueous Chemistry of the VanadiumIII (VIII) and the VIII-Dipicolinate Systems and a Comparison of the Effect of Three Oxidation States of Vanadium Compounds on Diabetic Hyperglycemia in Rats", Inorganic Chemistry, vol. 44, pp. 5416-5427, 2005.

Crans et al., "Penetration of Negatively Charged Lipid Interfaces by the Doubly Deprotonated Dipicolinate", J. Org. Chem. vol. 73, pp. 9633-9640, 2008.

Crans et al., "Vanadium(IV) and vanadium(V) complexes of dipicolinic acid and derivatives. Synthesis, X-ray structure, solution state properties and effects in rats with STZ-induced diabetes", Inorganica Chimica Acta, vol. 356, pp. 365-378, 2003.

Crans, "Chemistry and insulin-like properties of vanadium(IV) and vanadium(V) compounds 1", Journal of Inorganic Biochemistry, vol. 80, pp. 123-131, 2000.

Hakimi et al., "Preparation, Structural and Spectroscopic Characterization of Vanadium(IV) and Vanadium(V) Complexes with Dipicolinic Acid", Z. Anorg. Allg. Chem., vol. 637, (14-15), pp. 2157-2162, 2011.

Jakusch et al., "V anadium(IV/V) speciation of pyridine-2,6-dicarboxylic acid and 4-hydroxy-pyridine-2,6-dicarboxylic acid complexes: potentiometry, EPR spectroscopy and comparison across oxidation states", Journal of Inorganic Biochemistry, vol. 95 pp. 1-13, 2003.

Levina et al., "Reactivity—activity relationships of oral antidiabetic vanadium complexes in gastrointestinal media: an X-ray absorption spectroscopic study", Royal Society of Chemistry, Metallomics, vol. 6, pp. 1880-1888, 2014.

Reul et al., "Effects of vanadium complexes with organic ligands on glucose metabolism: a comparison study in diabetic rats", British Journal of Pharmacology, vol. 126, pp. 467-477, 1999.

Saboktakin et al., "pH Sensitive Chitosan-based Supramolecular Gel for Oral Drug Delivery of Insulin", J Mol Genet Med., vol. 9, Issue 2, 2015.

Sakurai and Yasui, "Structure-Activity Relationship of Insulinomimetic Vanadyl-Picolinate Complexes in View of Their Clinical Use", The Journal of Trace Elements in Experimental Medicine, vol. 6, pp. 269-280, 2003.

Scior et al., "Why Antidiabetic Vanadium Complexes are Not in the Pipeline of "Big Pharma" Drug Research? A Critical Review", Current Medicinal Chemistry, vol. 23, pp. 2874-2891, 2016.

Thompson et al., "Preparation and characterization of vanadyl complexes with bidentate maltol-type ligands; in vivo comparisons of anti-diabetic therapeutic potential", J Biol Inorg Chem, vol. 8, pp. 66-74, 2003.

Yilmaz, "Layer-by-layer hyaluronic acid/chitosan polyelectrolyte coated mesoporous silica nanoparticles as pH-responsive nanocontainers for optical bleaching of cellulose fabrics", Carbohydrate Polymers, vol. 146, pp. 174-180, 2016.

* cited by examiner

*P<0.05

*P<0.05

*P<0.05

*P<0.05

*P<0.05

*P<0.05

*P<0.05

*P<0.05

*P<0.05

*P<0.05

*P<0.05

*P<0.05

*P<0.05

*P<0.05

*P<0.05

*P<0.05

*P<0.05

*P<0.05

VANADIUM INSULIN-MIMETICS, METHODS OF PREPARATION, AND METHODS FOR TREATMENT OF DIABETES

This application is a Continuation application of PCT International Application No. PCT/TT2018/000,001 filed on Jun. 1, 2018, which claims priority under 35 U.S.C. § 119 on Patent Application No. 62/514,254 filed in the United States on Jun. 2, 2017, the entire contents of each of which are hereby incorporated by reference.

TECHNICAL FIELD

The present invention relates to novel insulin mimetics which are useful in the treatment of diabetes, in particular Type II diabetes. The invention further relates to compositions and combinations comprising these compounds and methods for their delivery and use in the treatment of diabetes, particularly Type II diabetes.

BACKGROUND

Diabetes mellitus (DM) is a metabolic disease arising from either the body's pancreas not being able to produce enough insulin or from the cells of the body not properly responding to the insulin produced. DM is categorized in two major classes: Type I and Type II. Type I DM, also known as immune-mediated diabetes was previously classified as insulin dependent DM or juvenile-onset diabetes. It occurs as a result of a cellular-mediated autoimmune destruction of the pancreatic beta-cells, which may be either genetically or environmentally influenced. Type II DM, previously classified as non-insulin dependent DM or adult onset diabetes, encompasses subjects who can either be predominantly insulin resistant or persons who display insulin secretory defects. In other words, the body either resists the effects of insulin or it does not produce adequate insulin to maintain a normal glucose level.

The first line of treatment for Type II DM is dietary therapy and exercise. When these therapies fail to return adequate glycaemic control, oral agents are used to either stimulate insulin production or increase insulin sensitivity. At this time, approved oral agents fall into several categories, for instance sulfonylureas (e.g Gliclazide), biguanides (e.g. Metformin), alpha-glycosidase inhibitors (e.g. Precose), thiazolidinediones (e.g. Avandia), meglitinides (e.g. Prandin), and dipeptidyl-pepidase IV (DPP-4) inhibitors (e.g. Sitagliptin).

Yet some studies suggest that particular metals can also have a positive effect on treatment, such as cobalt (Crans et al. (2003) *Inorg Chim Acta* 356:365-378), zinc and chromium (Katada et al. (2008) *J Biollnorgc Chem* 13(2): 249-255 and Wang et al. (2013) Organometallics 32:4882-489), and vanadium (Crans et al. (2003) *Inorg Chim Acta* 356:365-378; Rao et al. (2014) *J. Control Release* 193:174-187); and Kumar et al. (2014) *Langmuir* 30:4540-4544). In particular, organic vanadium complexes (peroxovanadiums, aka "pVs") have been shown to be insulin-mimetics (Thompson et al. (1999) *Chem Rev* 99(9):2561-72; Srivastava and Mehdi (2005) *Diabetic Med* 22(1):2-13; Peters et al. (2003) *J Inorg Biochem* 96:321-330; Willsky et al. (2011) *Coordin Chem Rev* 255:2258-2269).

Vanadium exists in several valence states (−1, +1, +2, +3, +4, +5), with vanadyl (+4; "IV") and vanadate (+5; "V") forms exhibiting agonistic activity in biological systems. Vanadium IV is an inorganic compound with the formula $VO_2$ and is a dark blue solid. Solid state vanadium IV is capable of being combined with a few synthetic ligands (Kumar et al. (2014) *Langmuir* 30:4540-4544). Vanadium IV oxide is amphoteric. Tetravalent vanadium forms complexes with several ligands, but vanadium IV is unstable in the absence of a reducing agent at a neutral pH. The most common intracellular form is vanadium IV.

Vanadium V has the formula $V_2O_5$ and is a yellowish-red powder that is slightly soluble in water. Vanadium V exhibits stereo-chemical flexible-coordination geometry ranging from tetrahedral and octahedral to trigonal pyramidal and pentagonal bipyramidal. Extracellular body fluids are dominated by the pentavalent form of vanadium.

Pyridine-2,6-dicarboxylic acid (commonly referred to as dipicolinic acid or "dipic") is a suitable metal ion ligand for complexing with vanadium and has been investigated in detail. In its free state, in addition to being nontoxic, dipicolinic acid has insignificant phosphatase or insulin-like activity (see, for example, Crans et al. (2003) *Inorg Chim Acta* 356:365-378). However, the dipicolinic acid—vanadium complex, while thermodynamically stable at acid pH, has some pH-dependent kinetic lability. Consequently, additional ligand-vanadium complexes are needed that have improved stability and lability patterns.

Yet despite their impressive anti-diabetic properties, vanadium compounds have been associated with several toxic effects, the most common being diarrhea, decreased fluid and food uptake, dehydration and reduced body weight (see, for example, Domingo et al. (1995) *Mol Cell Biochem* 153:233-240 and Domingo et al. (2002) *Biol Trace Elem Res* 88:97-112). While in some cases this has been due to impurities associated with the vanadium complexes, which have proved recalcitrant to purification systems (Baran (2003) *Braz. Chem. Soc.* 14 (6):878-888), a need remains for reducing overall vanadium compound/drug consumption and side-effects by depositing the active agent at the target site in dosages that are within the therapeutic range, but well under the toxic levels.

One way of accomplishing delivery of drugs to specific cells, thereby reducing toxicity, is through use of nanoparticles. Here, efficacy of drug delivery is largely based upon: (a) efficient encapsulation of the drugs, (b) successful delivery of the drug to the targeted region of the body, and (c) successful release of the drug. Currently being used are: gold nanoshells (Soni et al (2013) *Int J Hyperthermia* 29(1):87-97), liposomes (Bertrand et al. (2010) *ACS Nano* 4(12): 7552-7558), magnetic nanoparticles (Lee et al. (2014) *Nano Letters* 14(1): 1-5), polymeric nanocomposites/nanotubes (Lalwani et al. (2013) *Biomacromolecules* 14(3): 900-9 and Lalwani et al. (2013) *Acta Biomater* 9(9):8365-8373) colloidal carbon spheres (Sun and Li (2004) *Angew Chem* 43(5):597-601), carbon nanospheres (Selvi et al. (2008) *Nano Letters* 8(10):3182-3188 and Selvi et al. (2012) *J Nanobiotech* 10(1):33-35), $TiO_2$ nanoparticles (Mehranpour et al. (2012) *Proc 4$^{th}$ International Conference of Nanostructures* (1): 1710-1712), and mesoporous silica nanoparticles (Kumar et al. (2014) *Langmuir* 30:4540-4544). While these delivery systems exist, problems remain for avoiding toxicity from drug dosages that are increased to compensate for drug deterioration in the acidic stomach environment before the effective release of sufficient dosages in the intestines where the drug is absorbed.

Consequently, there remains a pressing need for new compounds amenable to oral treatment of diabetes, especially Type II diabetes, that have reduced toxicity and improved delivery, with efficient and effective release kinetics.

BRIEF SUMMARY OF THE INVENTION

In one embodiment, the invention provides compounds represented by Formula 1:

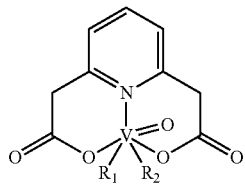

Formula 1 wherein:

$R_1$ and $R_2$ are independently $(C_1-C_{18})$ alkyl, $NH_2$—COH—CHOH, $NH_2$—$(C_1-C_{18})$alkyl, $NH_2$—$(C_1-C_{18})$ alkyl-$NH_2$, =O, aryl, substituted aryl, or a monodentate ligand, wherein each monodentate ligand is halo or $OH_2$;

or a pharmaceutically acceptable salt thereof.

In one embodiment, a compound of Formula 1 is represented by Complex 1:

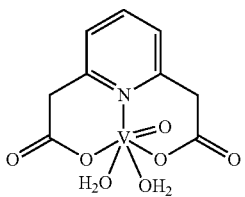

Complex 1

In yet another embodiment, the invention provides compounds represented by Formula 2:

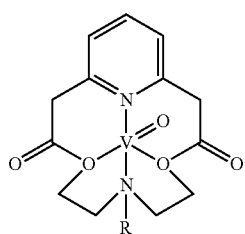

Formula 2 wherein:

R is H, $(C_1-C_{18})$ alkyl, aryl, or substituted aryl;

or a pharmaceutically acceptable salt thereof.

Still another aspect of the invention compounds represented by Formula 3:

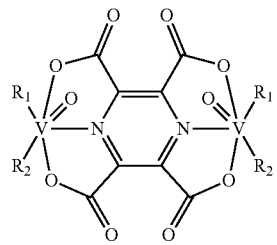

Formula 3 wherein:

$R_1$ and $R_2$ are independently selected from $H_2O$, $(C_1-C_{18})$ alkyl, aryl, substituted aryl; or a pharmaceutically acceptable salt thereof.

Yet another aspect of the invention provides a crystal of a compound of Formula 1 wherein:

$R_1$ and $R_2$ are $H_2O$;

or a pharmaceutically acceptable salt thereof.

A further aspect of the invention provides a crystal of a compound of Formula 2 wherein:

R is H, $(C_1-C_{18})$ alkyl, or hydroxyl-substituted aryl;

or a pharmaceutically acceptable salt thereof.

A still further aspect of the invention provides a crystal of a compound of Formula 3 wherein:

$R_1$ and $R_2$ are independently selected from $H_2O$, $(C_1-C_{18})$ alkyl, aryl, substituted aryl;

or a pharmaceutically acceptable salt thereof.

Another aspect of the invention provides a compound of Formula 1 and/or Formula 2 and/or Formula 3, or a pharmaceutically acceptable salt thereof, as a medicament.

Also within the scope of this invention is the use of a compound of Formula 1 and/or Formula 2 and/or Formula 3, or a pharmaceutically acceptable salt thereof, for the manufacture of a medicament for the treatment of DM.

Included within the scope of this invention is a pharmaceutical composition comprising a compound of Formula 1 and/or Formula 2 and/or Formula 3, or a pharmaceutically acceptable salt thereof, and a pharmaceutically acceptable carrier.

According to a further aspect of this embodiment the pharmaceutical composition according to this invention further comprises a therapeutically effective amount of at least one other DM agent.

The invention also provides the use of a pharmaceutical composition as described hereinabove for the treatment of DM in a human being having, or at risk of having, the disease.

Another aspect of the invention provides a method of treating DM in a human being by administering to the human being an effective amount of a compound of the invention, a pharmaceutically acceptable salt thereof, or a composition as described above, alone or in combination with at least one other DM agent, administered together or separately.

Still another aspect of the invention relates to a method of delivering a compound of Formula 1 and/or Formula 2 and/or Formula 3 via a nanoparticle.

Yet another aspect of the invention relates to a method of delivering a compound of Formula 1 and/or Formula 2 and/or Formula 3 via a hydrogel.

An additional aspect of this invention refers to an article of manufacture comprising a composition effective to treat DM; and packaging material comprising a label which indicates that the composition can be used to treat DM;

wherein the composition comprises a compound of Formula 1 and/or Formula 2 and/or Formula 3 or a pharmaceutically acceptable salt thereof.

BRIEF DESCRIPTION OF THE DRAWINGS

FIG. 1A: Reaction Scheme 1; FIG. 1B: Reaction Scheme 2; FIG. 1C: Reaction Scheme 3.

FIG. 2A: ORTEP diagram showing single crystal representation of Complex 1; FIG. 2B: ball and stick 3-D model of Complex 1 at pH 7.4; FIG. 2C: PXRD of Complex 1; FIG. 2D: UV-Vis spectrum of Complex 1.

FIG. 3A: SEM Image of uncoated MCM-41; FIG. 3B: TEM image of uncoated MCM-41; FIG. 3C: $N_2$ Adsorption/Desorption Plot; FIG. 3D: PXRD Pattern; FIG. 3E: DLS data showing correlogram of MCM-41 particles; with corresponding size distribution FIG. 3F.

FIG. 4A: Percentage loading of the Complex 1 into MCM-41 (inset showing the photograph of Complex 1 loaded MCM-41); FIG. 4B: $N_2$ Adsorption/Desorption studies, confirming adsorption for MCM+Complex 1.

FIG. 8A: SEM image of coated nanoparticles; FIG. 8B: TEM image of coated nanoparticles; note the obscurance of the nanoparticle channels that initially visible in the uncoated nanoparticles (stripes).

FIG. 10A: Graph depicting trend over time. FIG. 10B: Bar showing final results. $P<0.05$ analysis via One-way analysis of variance (ANOVA) using Tukey HSD post hoc.

FIG. 17A: Graph depicting trend over time. FIG. 17B: Bar showing final results. $P<0.05$ analysis via One-way analysis of variance (ANOVA) using Tukey HSD post hoc.

Figure 1A:
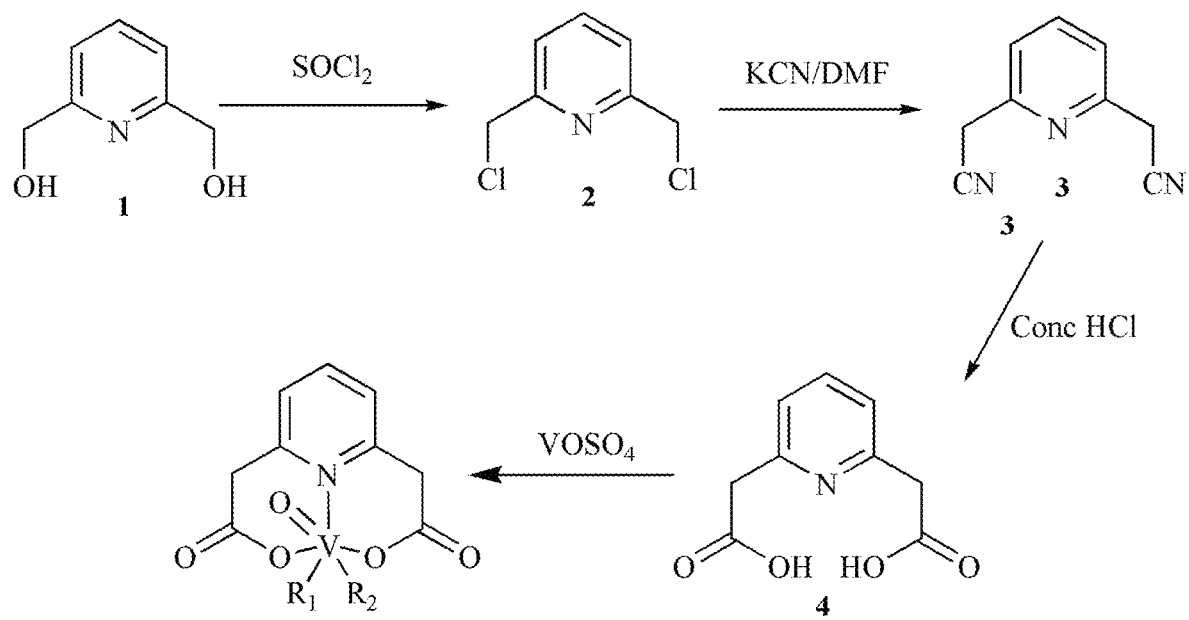
FIGS. 1A-1C: Synthetic Approach for Formula 1 and Formula 2 Complexes.

Table 1 lists the data collection and refinement statistics.

Table 2 lists the crystallographic coordinate transformation data.

DETAILED DESCRIPTION OF THE INVENTION

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-18}$-alkyl means an alkyl group or radical having 1 to 18 carbon atoms. In general, for groups comprising two or more subgroups, the first named subgroup is the radical attachment point, for example, the substituent "$C_{1-3}$-alkyl-aryl" means an aryl group which is bound to a $C_{1-3}$-alkyl-group, with the $C_{1-3}$-alkyl-group bound to the core. Unless specifically stated otherwise, for groups comprising two or more subgroups, the substituent may be attached to either subgroup.

If a compound of the present invention is depicted in the form of a chemical name and as a formula, in case of any discrepancy the formula shall prevail. An asterisk or the designation "-" may be used in sub-formulas to indicate the bond which is connected to the core molecule as defined.

Unless specifically indicated, throughout the specification and the appended claims, a given chemical formula or name shall encompass tautomers and all stereo, optical, and geometrical isomers (e.g. enantiomers, diastereomers, E/Z isomers, atropisomers) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as, for instance, hydrates including solvates of the free compounds or solvates of a salt of the compound.

One skilled in the art would know how to separate, enrich, or selectively prepare the enantiomers of the compounds of the present invention. Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, but are not limited to, chromatography using chiral stationary phases, enantioselective host-guest complexation, resolution or synthesis using chiral auxiliaries, enantioselective synthesis, enzymatic and non-enzymatic kinetic resolution, or spontaneous enantioselective crystallization. Such methods are disclosed generally in Chiral Separation Techniques: A Practical Approach (2$^{nd}$ Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including, but not limited to, GC, HPLC, CE, or NMR, and assignment of absolute confirmation and conformation, including but not limited to CD, ORD, X-ray crystallography, or NMR.

The term "halo" generally denotes fluorine, chlorine, bromine, and iodine.

"$C_m$-$C_n$ alkyl" on its own or in composite expressions such as $C_m$—$C_n$ haloalkyl, $C_m$-$C_n$ alkylcarbonyl, $C_m$—$C_n$ alkylamine, etc. represents a straight or branched aliphatic hydrocarbon radical having the number of carbon atoms designated, e.g. $C_1$-$C_4$alkyl means an alkyl radical having from 1 to 4 carbon atoms. $C_1$-$C_{18}$ alkyl has a corresponding meaning, including also all straight and branched chain isomers of pentyl and hexyl.

Preferred alkyl radicals for use in the present invention are $C_1$-$C_{18}$ alkyl, including methyl, ethyl, n-propyl, isopropyl, n-butyl, isobutyl, sec-butyl, tert-butyl, n-pentyl, n-hexyl, n-dodecyl, n-hexadecyl and n-octadecyl especially $C_1$-$C_4$ alkyl such as methyl, ethyl, n-propyl, isopropyl, t-butyl, n-butyl and isobutyl. Methyl and isopropyl are typically preferred. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(=O)-alkyl, —O—C(=O)-aryl, —O—C(=O)-cycloalkyl, —C(=O) OH and —C(=O)O-alkyl. It is generally preferred that the alkyl group is unsubstituted, unless otherwise indicated.

"$C_2$-$C_n$ alkenyl" represents a straight or branched aliphatic hydrocarbon radical containing at least one carbon-carbon double bond and having the number of carbon atoms designated, e.g. $C_2$-$C_4$ alkenyl means an alkenyl radical having from 2 to 4 carbon atoms; $C_2$-$C_6$ alkenyl means an alkenyl radical having from 2 to 6 carbon atoms. Non-limiting alkenyl groups include ethenyl, propenyl, n-butenyl, 3-methylbut-2-enyl, n-pentenyl and hexenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(=O)-alkyl, —O—C(=O)-aryl, —O—C(=O)-cycloalkyl, —C(=O)OH and —C(=O)O-alkyl. It is generally preferred that the alkenyl group is unsubstituted, unless otherwise indicated.

"$C_2$-$C_n$ alkynyl" represents a straight or branched aliphatic hydrocarbon radical containing at least one carbon-carbon triple bond and having the number of carbon atoms designated, e.g. $C_2$-$C_4$ alkynyl means an alkynyl radical having from 2 to 4 carbon atoms; $C_2$-$C_6$ alkynyl means an alkynyl radical having from 2 to 6 carbon atoms. Non-limiting alkenyl groups include ethynyl, propynyl, 2-butynyl and 3-methylbutynyl pentynyl and hexynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(=O)-alkyl, —O—C(=O)-aryl, —O—C(=O)-cycloalkyl, —C(O)OH and —C(O)O-alkyl. It is generally preferred that the alkynyl group is unsubstituted, unless otherwise indicated.

The term "$C_m$-$C_n$ haloalkyl" as used herein represents $C_m$-$C_n$ alkyl wherein at least one C atom is substituted with a halogen (e.g. the $C_m$-$C_n$ haloalkyl group may contain one to three halogen atoms), preferably chloro or fluoro. Typical haloalkyl groups are $C_1$—C; haloalkyl, in which halo suitably represents fluoro. Exemplary haloalkyl groups include fluoromethyl, difluromethyl and trifluoromethyl.

The term "$C_m$-$C_n$ hydroxyalkyl" as used herein represents $C_m$-$C_n$ alkyl wherein at least one C atom is substituted with one hydroxy group. Typical $C_m$-$C_n$ hydroxyalkyl groups are $C_m$-$C_n$ alkyl wherein one C atom is substituted with one hydroxy group. Exemplary hydroxyalkyl groups include hydroxymethyl and hydroxyethyl.

The term "$C_m$-$C_n$ aminoalkyl" as used herein represents $C_m$-$C_n$ alkyl wherein at least one C atom is substituted with one amino group. Typical $C_m$-$C_n$ aminoalkyl groups are $C_m$-$C_n$alkyl wherein one C atom is substituted with one amino group. Exemplary aminoalkyl groups include aminomethyl and aminoethyl.

The term "$C_m$-$C_n$ alkylene" as used herein represents a straight or branched bivalent alkyl radical having the number of carbon atoms indicated. Preferred $C_m$-$C_n$ alkylene radicals for use in the present invention are $C_1$-$C_3$ alkylene. Non-limiting examples of alkylene groups include —CH$_2$—, —CH$_2$CH$_2$—, —CH$_2$CH$_2$CH$_2$—, —CH(CH$_3$)CH$_2$—, —CH(CH$_3$)— and —CH(CH(CH$_3$)$_2$)—.

The term "Me" means methyl, and "MeO" means methoxy.

The term "$C_m$-$C_n$ alkylcarbonyl" represents a radical of the formula $C_m$-$C_n$ alkyl-C(=O)— wherein the $C_m$-$C_n$ alkyl moiety is as defined above. Typically, "$C_m$-$C_n$ alkylcarbonyl" is $C_1$-$C_{18}$ alkyl-C(=O)—.

"$C_m$-$C_n$ alkoxy" represents a radical $C_m$-$C_n$ alkyl-O— wherein $C_m$-$C_n$ alkyl is as defined above. Of particular interest is $C_1$-$C_4$ alkoxy which includes methoxy, ethoxy, n-propoxy, isopropoxy, t-butoxy, n-butoxy and isobutoxy. Methoxy and isopropoxy are typically preferred. $C_1$-$C_6$ alkoxy has a corresponding meaning, expanded to include all straight and branched chain isomers of pentoxy and hexoxy.

The term "$C_m$-$C_n$ alkoxycarbonyl" represents a radical of the formula $C_m$-$C_n$ alkoxy-C(=O)— wherein the $C_m$-$C_n$ alkoxy moiety is as defined above. Typically, "$C_m$-$C_n$ alkoxycarbonyl" is $C_1$-$C_6$ alkoxy-C(=O)—.

The term "amino" represents the radical —NH$_2$.

The term "aryl" as used herein, either alone or in combination with another radical, denotes a carbocyclic aromatic monocyclic group.

The term "carbocycly" or "carbocycle" as used herein, either alone or in combination with another radical, means a mono-, bi-, or tricyclic ring structure consisting of 3 to 14 carbon atoms. The term "carbocycly" or "carbocycle" refers to fully saturated and aromatic ring systems and partially saturated ring systems. The term carbocycly" or "carbocycle" encompasses fused, bridged, and spirocyclic systems.

The term "heterocycloalkyl" represents a stable saturated monocyclic 3-7 membered ring containing 1-3 heteroatoms independently selected from O, S and N. In one embodiment, the stable saturated monocyclic 3-7 membered ring contains 1 heteroatom selected from O, S and N. In a second embodiment, the stable saturated monocyclic 3-7 membered ring contains 2 heteroatoms independently selected from O, S and N. In a third embodiment, the stable saturated monocyclic 3-7 membered ring contains 3 heteroatoms independently selected from O, S and N. The stable saturated monocyclic 3-7 membered ring containing 1-3 heteroatoms independently selected from O, S and N may typically be a 5-7 membered ring, such as a 5 or 6 membered ring. A heterocycloalkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(=O)-alkyl, —O—C(=O)-aryl, —O—C(=O)-cycloalkyl, —C(=O)OH and —C(=O)O-alkyl. It is generally preferred that the heterocycloalkyl group is unsubstituted, unless otherwise indicated.

The term "heteroaryl" represents a stable mono or bicyclic aromatic ring system containing 1-4 heteroatoms independently selected from O, S and N, each ring having 5 or 6 ring atoms. In one embodiment of the invention the stable mono or bicyclic aromatic ring system contains one heteroatom selected from O, S and N, each ring having 5 or 6 ring atoms. In a second embodiment of the invention the stable mono or bicyclic aromatic ring system contains two heteroatoms independently selected from O, S and N, each ring having 5 or 6 ring atoms. In a third embodiment, the stable mono or bicyclic aromatic ring system contains three heteroatoms independently selected from O, S and N, each ring having 5 or 6 ring atoms. In a fourth embodiment, the stable mono or bicyclic aromatic ring system contains four heteroatoms independently selected from O, S and N, each ring having 5 or 6 ring atoms.

The term "$C_3$-$C_n$ cycloalkyl" represents a cyclic monovalent alkyl radical having the number of carbon atoms indicated, e.g. $C_3$-$C_7$ cycloalkyl means a cyclic monovalent alkyl radical having from 3 to 7 carbon atoms. Preferred cycloalkyl radicals for use in the present invention are $C_3$-$C_4$alkyl i.e. cyclopropyl and cyclobutyl. A cycloalkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(=O)-alkyl, —O—C(=O)-aryl, —O—C(=O)-cycloalkyl, —C(=O)OH and —C(=O)O-alkyl. It is generally preferred that the cycloalkyl group is unsubstituted, unless otherwise indicated.

The term "amino $C_m$-$C_n$ alkyl" represents a $C_m$-$C_n$ alkyl radical as defined above which is substituted with an amino group, i.e. one hydrogen atom of the alkyl moiety is replaced by an NH$_2$-group. Typically, "amino $C_m$-$C_n$ alkyl" is amino $C_1$-$C_6$ alkyl.

The term "amino $C_m$-$C_n$ alkylcarbonyl" represents a $C_m$-$C_n$ alkylcarbonyl radical as defined above, wherein one hydrogen atom of the alkyl moiety is replaced by an NH$_2$-group. Typically, "amino $C_m$-$C_n$ alkylcarbonyl" is amino $C_1$-$C_6$ alkylcarbonyl. Examples of amino $C_m$-$C_n$ alkylcarbonyl include but are not limited to glycyl: C(=O)CH$_2$NH$_2$, alanyl: C(=O)CH(NH$_2$)CH$_3$, valinyl: C=OCH(NH$_2$)CH(CH$_3$)$_2$, leucinyl: C(=O)CH(NH$_2$)(CH$_2$)$_3$CH$_3$, isoleucinyl: C(=O)CH(NH$_2$)CH(CH$_3$)(CH$_2$CH$_3$) and norleucinyl: C(=O)CH(NH$_2$)(CH$_2$)$_3$CH$_3$, and the like. This definition is not limited to naturally occurring amino acids.

As used herein, the term "(=O)" forms a carbonyl moiety when attached to a carbon atom. It should be noted that an atom can only carry an oxo group when the valency of that atom so permits.

As used herein, the radical positions on any molecular moiety used in the definitions may be anywhere on such a moiety as long as it is chemically stable. When any variable present occurs more than once in any moiety, each definition is independent.

The term "solvates" covers any pharmaceutically acceptable solvates that the compounds of Formula 1 and/or Formula 2 and/or Formula 3, as well as the salts thereof, are able to form. Such solvates are for example hydrates, alcoholates, e.g. ethanolates, propanolates, and the like, especially hydrates.

The term "medium rings" denotes rings having 8-11 atoms.

The term "macrocycle" covers any ring system of 12 or more atoms, such as rings having $C_{12}$, $C_{13}$, $C_{14}$, $C_{15}$, $C_{16}$, $C_{17}$, $C_{18}$, $C_{19}$, $C_{20}$, etc.

The term "prodrug" as used herein denotes a compound that is a drug precursor which upon administration to a subject are readily convertible in vivo by metabolic and/or chemical processes to yield the active compound.

The term "hydrogel" as used herein means a two- or multi-component system consisting of a three-dimensional network of polymer chains and water that fills the space between macromolecules. Hydrogels may be synthesized in a number of "classical" chemical ways, which include one-step procedures like polymerization and parallel cross-linking of multifunctional monomers, as well as multiple step procedures involving syntheses of polymer molecules having reactive groups and their subsequent cross-linking. Examples of such polymers include, but are not limited to: Hyaluronic Acid, Dextran Sulfate and Chitosan.

The pharmaceutically acceptable addition salts comprise the therapeutically active non-toxic acid and base addition salt forms of the compounds of Formula 1 and/or Formula 2 and/or Formula 3. Of interest are also the free, i.e. non-salt, forms of the compounds of Formula 1 and/or Formula 2 and/or Formula 3.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxylbutanedioic acid), tartaric, citric, methanesulfonic, ethanesulfonic, benzenesulfonic, p-toluenesulfonic, cyclamic, salicylic, p-aminosalicylic, pamoic, and the like acids. Conversely said salt forms can be converted by treatment with an appropriate base into the free base form.

The compounds of Formula 1 and/or Formula 2 and/or Formula 3 containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine, and the like.

Some of the compounds of Formula 1 and/or Formula 2 and/or Formula 3 may also exist in their tautomeric form. For example, tautomeric forms of amide groups (—C(=O)—NH—) are iminoalcohols (—C(OH)=N—), which can become stabilized in rings with aromatic character. Such forms, although not explicitly indicated in the structural formulae represented herein, are intended to be included within the scope of the present invention.

Whenever used herein, the term "compounds of Formula 1 and/or Formula 2 and/or Formula 3", or "the compounds of the invention" or similar terms, it is meant to include the compounds of Formula 1 and/or Formula 2 and/or Formula 3 and subgroups of compounds of Formula 1 and/or Formula 2 and/or Formula 3, including the possible stereochemically isomeric forms, and their pharmaceutically acceptable salts and solvates.

The term "solvates" covers any pharmaceutically acceptable solvates that the compounds of Formula 1 and/or Formula 2 and/or Formula 3 as well as the salts thereof, are able to form. Such solvates are for example hydrates, alcoholates, e.g. ethanolates, propanolates, and the like, especially hydrates.

The term "structure coordinates" refers to mathematical coordinates derived from mathematical equations related to the patterns obtained on diffraction of a monochromatic beam of X-rays by the atoms (scattering centers) of a molecule of Complex 1 in crystal form. The diffraction data are used to calculate an electron density map of the repeating unit of the crystal. The electron density maps are used to establish the positions of the individual atoms within the unit cell of the crystal.

Those of skill in the art understand that a set of structure coordinates determined by X-ray crystallography is not without standard error. For the purpose of this invention, any set of structure coordinates that has a root mean square deviation of less than 1.5 Å when superimposed on the structure coordinates shall be considered identical.

Synthetic Approach for Formula 1 and Formula 2 Complexes

Figure 1B:
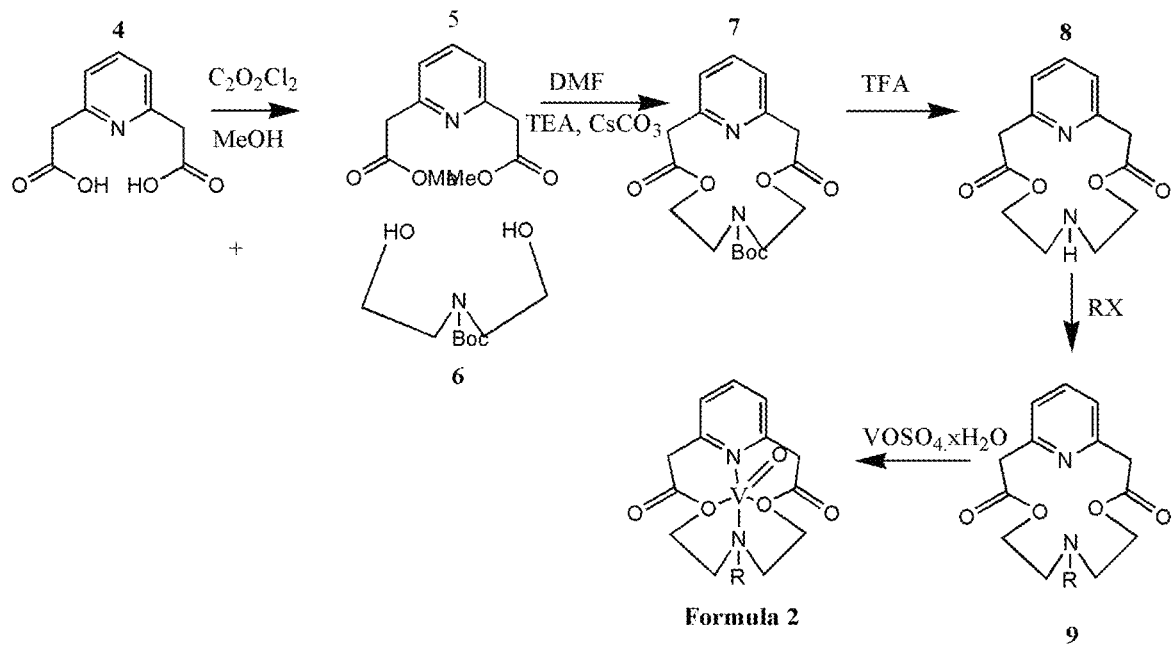
Figure 1C:
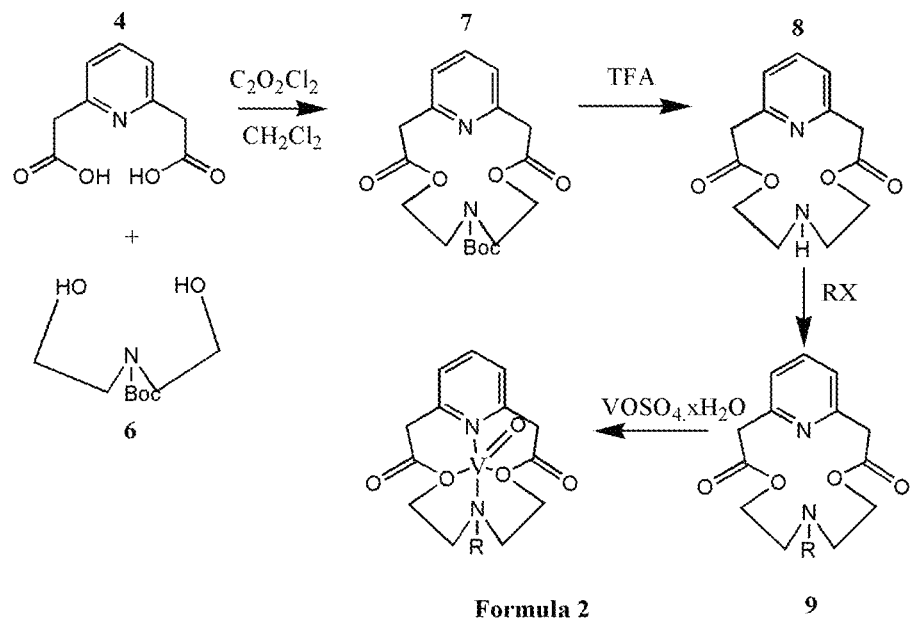
Figure 2A:
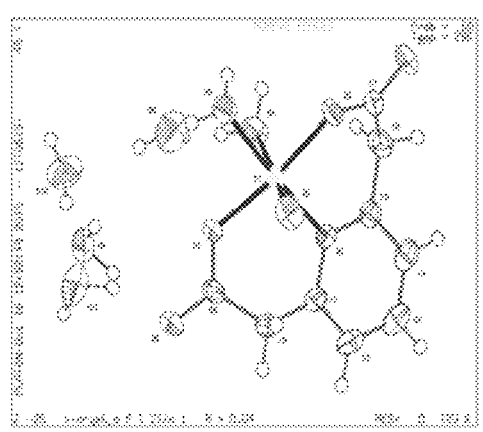
FIGS. 2A-2D.
Figure 2B:
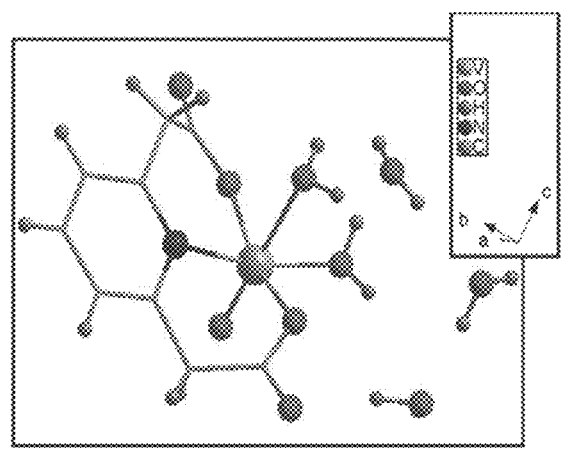
Figure 2C:
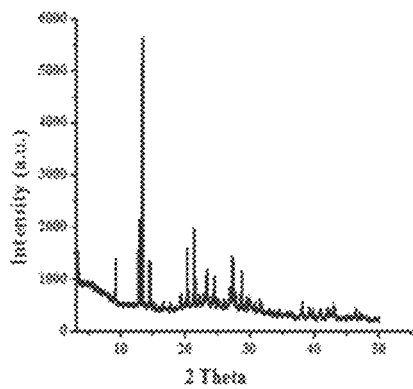
Figure 2D:
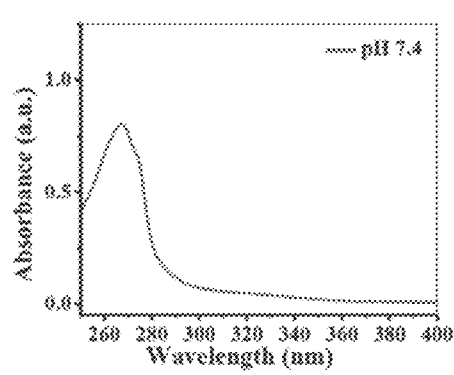
Figure 3A:
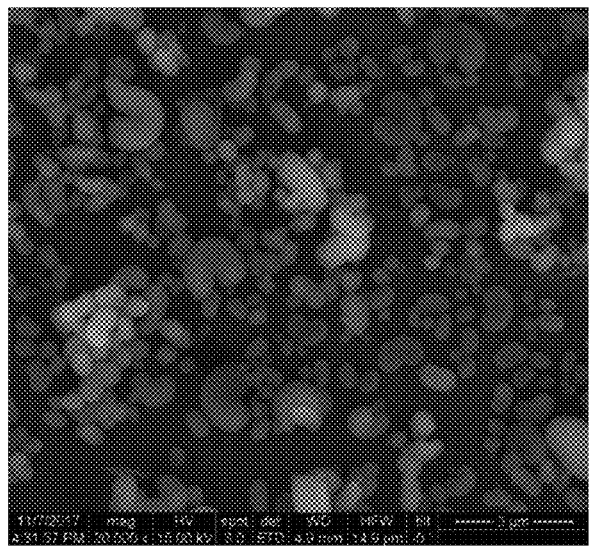
FIGS. 3A-3F.
Figure 3B:
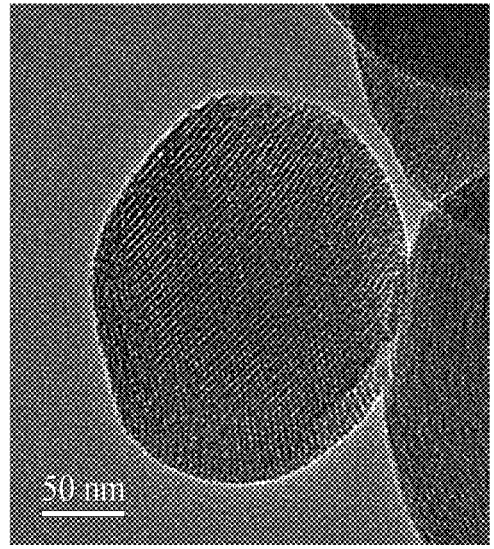
Figure 3C:
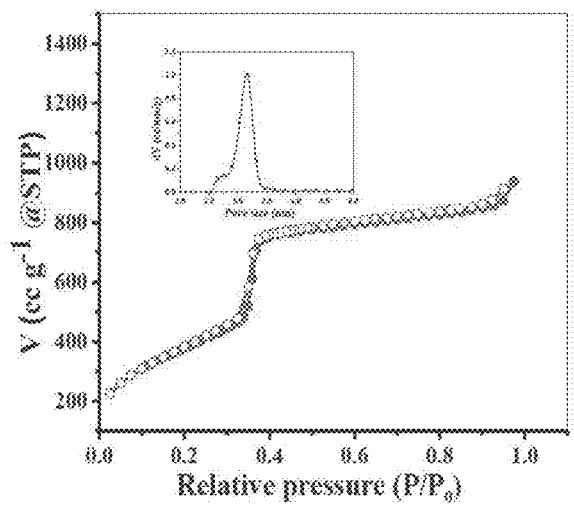
Figure 3D:
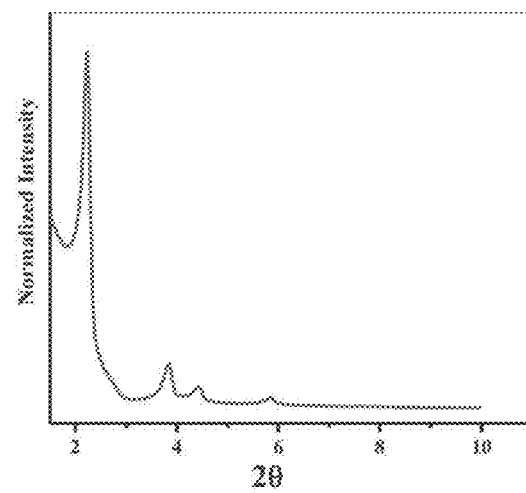
Figure 3E:
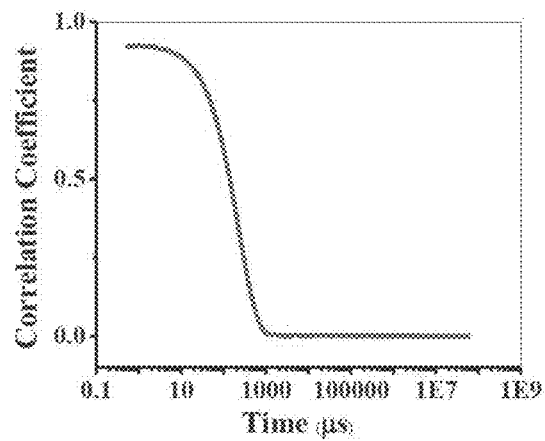
Figure 3F:
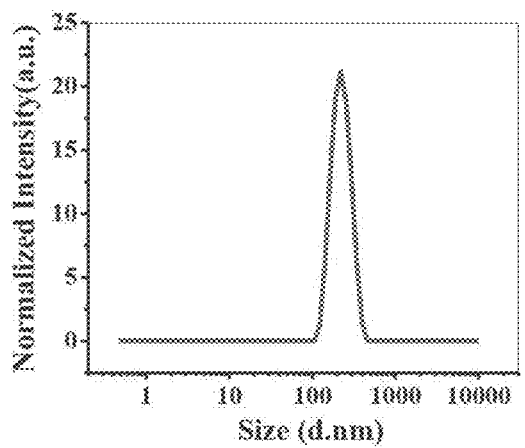

The syntheses of some of the complexes defined by Formula 1 and Formula 2 are illustrated in FIGS. 1A-1C and below. The retrosynthetic design of the target molecules (Reaction Schemes 1, 2 and 3) enabled the incorporation of 2, 6-pyridinediacetic acid (PDA), an analogue to the privileged ligand, pyridine-2,6-dipicolinic acid (dipic). Here, the extended carboxyl pendent arms of PDA facilitate a more stable chelation to the vanadyl ion as exemplified by Formula 1 or in the cyclic form (Formula 2), allowing the vanadyl ion to sit in a less sterically hindered environment as a "belt" rather than a "crown."

Reaction pathway to target ligand: 2,6-pyridine diacetic acid (4)

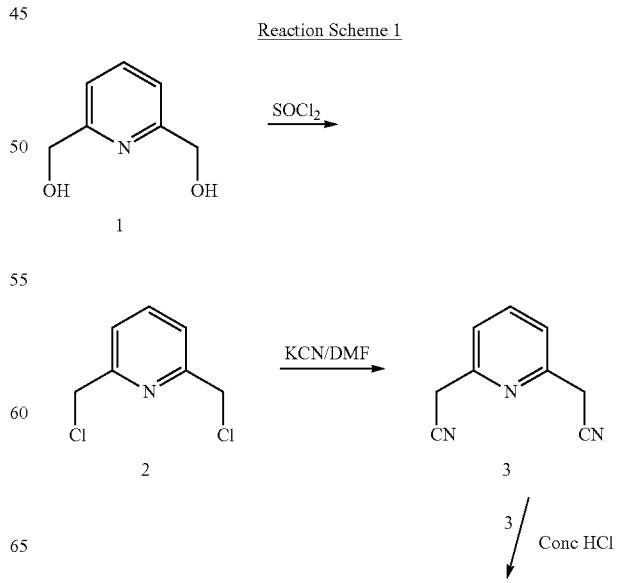

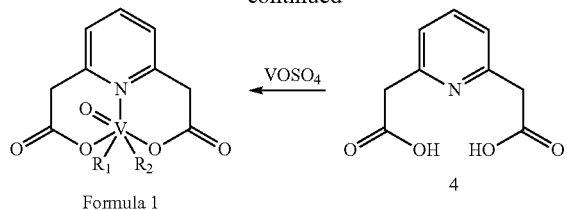

Formula 1

Reaction Scheme 1 shows the conversion of the starting material, 2,6-pyridine dimethanol (1) to 2,6-bis-chloromethyl pyridine (2). The carbon pendent arm of (2) was then extended via nucleophilic addition, to produce (6-cyanomethyl-pyridin-2-yl)-acetonitrile (3), which when hydrolyzed produces the target, 2,6 pyridine diacetic acid (4).

Synthesis of 2,6 bischloromethyl pyridine (2)

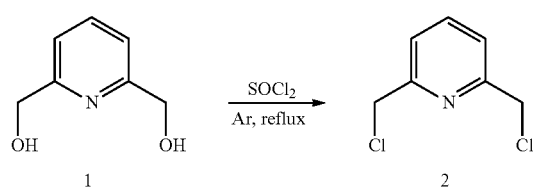 [SMILES: OCc1cccc(CO)n1 ; "SOCl2" ; ClCc1cccc(CCl)n1]

25 grams (179.7 mmol) of 2,6-pyridine dimethanol (1) was charged in 500 ml RB flask equipped with a large Teflon coated magnetic stirrer. A pressure equalizing funnel (PEF) was fitted into the flask and the entire system was purged with nitrogen for 15 minutes. 100 ml of thionyl chloride (SOCl$_2$) was then added dropwise to (1) at 0° C. over a period of 1 hour, while maintaining a positive flow of N$_2$ (g). After the addition step, the reaction mixture was refluxed for 4 hours under nitrogen. Excess SOCl$_2$ was removed via vacuum distillation after which the light yellow residue was dissolved in distilled water (100 ml) and 6 M HCl (100 ml). Upon addition of the water/HCl mixture, an insoluble dark brown sludge was observed and subsequently removed by gravity filtration. Neutralization of the filtrate with saturated NaHCO$_3$, yielded a white precipitate of 2,6-bis-chloromethyl pyridine (2).

The precipitate was suction filtered and dissolved in hot hexane (100 ml). The solution was decanted from a green sludge seen at the bottom of the beaker, reduced to 50 ml and then left overnight at 4° C. to crystallize. Crystals were harvested by suction filtration and dried under high vacuum.

(28.42 grams=[89.88%]). R$_f$ (100% DCM)=0.67. $^1$H NMR (CDCl$_3$): δ 4.65 (4H's, s), 7.43 (2H's, d, J=7.4), 7.75 (t, 1H, J=7.71). $^{13}$C NMR (CDCl$_3$): δ 46.37, 122.05, 138.09 and 156.29.

Synthesis of (6-Cyanomethyl-pyridin-2-yl)-acetonitrile (3)

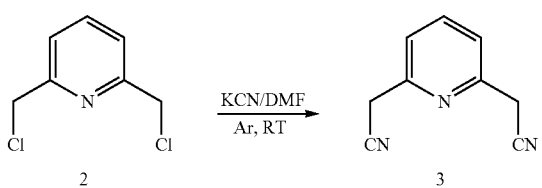 [SMILES: ClCc1cccc(CCl)n1 ; "KCN/DMF" ; N#CCc1cccc(CC#N)n1]

28.00 grams (159.1 mmoles) of 2,6-bis-chloromethylpyradine (2), 35 grams (537 mmoles) of KCN and DMF (500 ml) were charged into 1 L RB flask, equipped with a larger Teflon coated magnetic stirrer and left to stir at room temperature (RT) under nitrogen for 24 hours. After the elapsed time, the dark brown reaction mixture was suction filtered and DMF was removed by rotary evaporation to give a dark brown residue which solidified on cooling.

Dichloromethane (DCM) (100 ml) and a saturated solution of LiCl (100 ml) were poured into the RB flask containing the residue and stirred for 15 minutes. The organic layer was collected and the aqueous layer further extracted with DCM (3×25 ml). The organic layers were combined and dried over anhydrous sodium sulfate. The mixture was then suction filtered and the filtrate was reduced to dryness by rotary evaporation to give a dark brown crude product which also solidified on cooling.

The product, (6-cyanomethyl-pyridin-2-yl)-acetonitrile (3), was isolated via column chromatography using a DCM/Hexane (9:1) solvent system. Compound 3 eluted as a brick red band and upon rotary evaporation of the fraction, furnished a light brown amorphous solid.

(21.23 g=[84.95%]). R$_f$ (100% DCM)=0.42. $^1$H NMR (CDCl$_3$): δ 3.9 (4H's, s), δ 7.40 (2H's, d, J=7.41 Hz), 67.80 (t, 1H, J=7.79 Hz). $^{13}$C NMR: 6150.95, 138.84, 121.60, 116.74, 26.46. IR (cm$^{-1}$): 2255.97 CN stretch.

Synthesis of 6-carboxymethyl-pyradin-2-acetic acid (2,6 pyridine diacetic acid) (4)

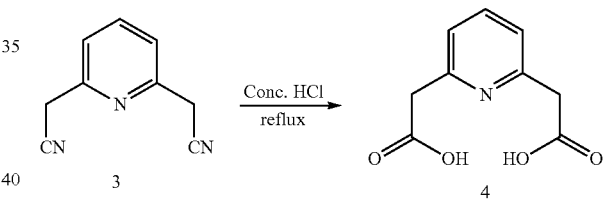

The Bombi et al. (2009; Polyhedron, 28(2): 327-335) procedure for the synthesis of PDA (4) was modified as stated below (Reaction Scheme 2). 21 grams (133.61 mmol) of (3) and concentrated HCl (400 ml) was placed in a 1 L RB flask equipped with a Teflon coated magnetic stirrer. The mixture was allowed to gently reflux for 18 hours and cooled to room temperature. The solvent was then removed under reduced pressure. The moss-green residue was dissolved in hot distilled water (500 ml) and decolorized with activated carbon (6.0 g).

After removal of the carbon via suction filtration, the pH of the light green solution was carefully adjusted to 2 by the dropwise addition of 1 M NaOH; when the target pH was achieved, the solution was seen to turn turbid at which point it was left to precipitate overnight at 4° C. The white precipitate was collected via suction filtration and characterized. A second batch of product was obtained by taking the filtrate, further adjusting it to pH 2, and then leaving it for 24 hours at 4° C. X-ray quality crystals were obtained via slow evaporation from deionized water.

(17.50 g=[67.31%] Melting point, 155-156° C. R$_f$(100% MeOH)=0.645. $^1$H NMR (D$_2$O): δ 4.0 (4H's, s], 7.71 (2H's, d, J=8.0 Hz), 8.36 (t, 1H, J=8.0 Hz). $^{13}$C NMR (D$_2$O): 6150.95, 138.84, 121.60, 116.74, 26.46. IR (cm$^{-1}$): 3237.23 cm$^{-1}$ (OH stretch), 1721 (C=O stretch).

Formula 1 is readily obtained by a simple one-to-one stoichiometric complexation reaction.

Synthesis of Complex 1 (Diaqua)(2,6-pyridine diacetyl-carboxylato)oxovanadium(IV), [V(IV)O(pyridine diacetate)(H$_2$O)$_2$]

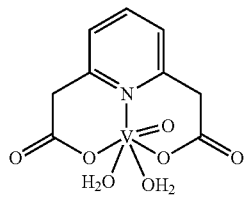

Complex 1

Vanadium Oxide Sulfate Hydrate (VOSO$_4$.xH$_2$O) (1.00 g, 4.6 mmol) was dissolved in 10 ml of deionized water and the pH of the resulting solution was increased to 4.00 with a 10% aqueous solution of sodium bicarbonate. To the resulting solution, a solution of 2,6-pyridinediacetic acid (4) (0.90 g in 50 ml Deionized water; 4.6 mmol) was added and the pH was maintained between 2.5-3.0 using 10% (aq) NaHCO$_3$. The reaction mixture was allowed to stir vigorously for a further 40 min (maintaining the pH between 2.5 and 3.0). The dark blue suspension was quickly filtered and the residue washed thoroughly with cold deionized water until all residue returned to solution.

Alternatively, Vanadium Oxide Sulfate Hydrate (VOSO$_4$.xH$_2$O) (1.66 g, 10.1 mmol) was dissolved in 100 ml of double distilled water and the pH of the resulting solution was increased to 4.00 with a 10% aqueous solution of sodium bicarbonate. In a separate beaker 2,6-pyridinediacetic acid (4) (1.99 g, 10.1 mmol) was dissolved in 80 ml hot (approximately 80-90° C.) double distilled water and quickly added to the vanadyl sulfate solution. The pH was maintained between 2.5-3.0 using 10% (aq) NaHCO$_3$ while stirring for a further 45 minutes. This optimized procedure reduced the reaction period from approximately 6 hours to 2 hours, due to the significantly smaller volume of filtrate that was required to be reduced in the proceeding product recovery step.

Preparation of Crystals

Crystals of Complex 1 were obtained as follows: The volume of the filtrate obtained from the synthesis set forth above was reduced under vacuum to approximately 5 ml and then left to crystalize at 0° C. for 12 hours prior to harvesting.

Alternatively, the approximately 5 ml solution of Complex 1 was eluted through a column of Sephadex G-25 and the second dark blue band collected. The volume of the eluent was reduced under vacuum distillation (maintaining the temperature below 50° C.) to 1 ml. The reduced solution was allowed to cool after which dark blue X-ray quality crystals were collected. Yield 1.05 g (77%).

However, those of skill in the art will appreciate that the aforesaid crystallization conditions can be varied, such as by using acidified Al$_2$O$_3$(Stationary Phase). In addition, crystals of Complex 1 can also be grown by a number of other techniques known in the art, including batch crystallization, vapor diffusion (e.g. sitting drop, hanging drop, or sandwich), microdialysis, membrane crystallization, or any other conventional method.

This is the first time crystals of Complex 1 as well as the structure of the molecule as determined therefrom have been provided.

Crystal Structure of Complex 1

Complex 1 was characterized via Single Crystal X-ray Diffraction, Powder X-ray Diffraction (PXRD), and UV-Vis Spectroscopy. Results are presented in FIGS. 2A-2D.

The Complex 1 data were collected from a crystal with dimensions of 2 mm×1 mm×1 mm using a Bruker D8 Venture diffractometer (Photon CMOS detector) equipped with a micro focus sealed tube X-ray source with graphite monochromatic Mo-Ka radiation ($\lambda$=0.71073 Å) operating at 50 kV and 1 mA[SC1] [SR2], with $\omega$ scan mode. The program SAINT was used for the integration of diffraction profiles and absorption corrections were made using the SADABS program. The structure was solved by direct methods followed by successive Fourier and difference Fourier syntheses. All the non-hydrogen atoms were refined anisotropically. Calculations were carried out using SIR-92, SHELXT, SHELXL-2014, SHELXL 97, SHELXS 97, PLATON, WinGX system, version 2014 and Olex2. Data statistics are given in Table 1.

TABLE 1

Data collection and refinement statistics

| Bond precision | C-C | 0.0026 A | |
|---|---|---|---|
| Wavelength | 0.71073 | | |
| Cell | a = 8.1263(2) | b = 13.2030(4) | c = 13.9854(4) |
| | alpha = 90 | beta = 101.439(1) | gamma = 90 |
| Temperature | 296 K | | |

Table 2 summarizes the crystallographic coordinate transformation data and the X-ray crystallography data sets of Complex 1.

TABLE 2

Crystallographic Coordinate Transformation Data

| | Calculated | Reported |
|---|---|---|
| Volume | 1470.71(7) | 1470.71(7) |
| Space group | P 21/n | P 1 21/n 1 |
| Hall group | -P 2yn | -P 2yn |
| Moiety formula | C9 H11 N O7 V, 3 (H2 O) | C9 H11 N O7 V, 3 (H2 O) |
| Sum Formula | C9 H17 N O10 V | C9 H17 N O10 V |
| Mr | 350.18 | 350.18 |
| Dx, g cm−3 | 10582 | 1.581 |
| Z | 4 | 4 |
| Mu (mm−1) | 0.723 | 0.723 |
| F000 | 724.0 | 725.8 |
| F000' | 725.68 | |
| H, k, lmax | 11, 18, 19 | 11, 18, 19 |
| Nref | 4156 | 4143 |
| Tmin, Tmax | 0.933, 0.971 | 0.709, 0.746 |
| Tmin' | 0.904 | |

Correction method=# Reported T Limits; Tmin=0.709 Tmax=0.746. Abs Corr=MULTI-SCAN. Data completeness=0.997. Theta (max)=29.620. R (reflections)=0.0351 (3540). wR2 (reflections)=0.1430 (1443). S=1.037. Npar=213.

Synthesis of Complexes 2-29

Additional complexes of Formula 1 can be formed, such as the following:

0.1 g (3.38×10$^4$ mols) Complex 1 was dissolved in 10 ml deionized water, at room temperature and the pH maintained between 3.0-4.0 using 1 M HCl (aq). The respective pendent group (in a mol ratio of 3×excess: Complex 1) was then added dropwise to the complex solution, with stirring to produce mono- or di-substituted products. The volume of the crude solution was then reduced to 5 ml and eluted through a gel packed column (Sephadex G-25) to retrieve the di-substituted and mono-substituted fractions of products in good purity. Isolation of either product can be through any suitable chromatographic technique including, but not limited to, column chromatography, high performance liquid chromatography (HPLC), and gas chromatography (GC).

Complex 2

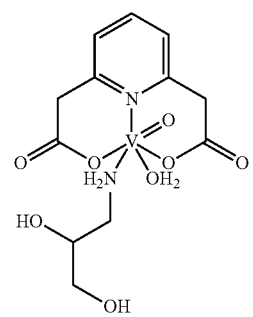

Complex 3

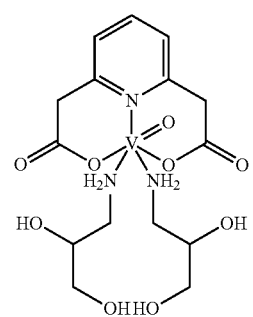

Complex 4

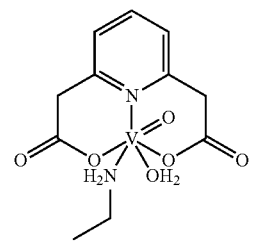

Complex 5

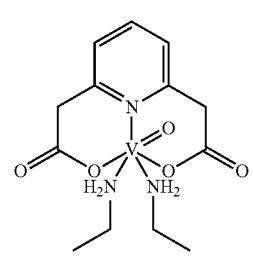

Complex 6

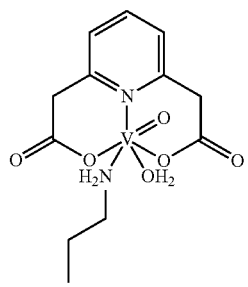

Complex 7

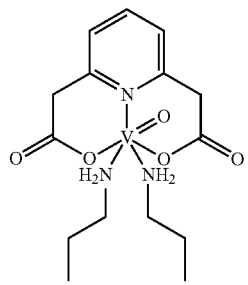

Complex 8

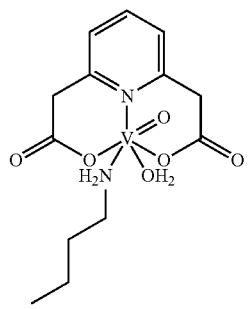

Complex 9

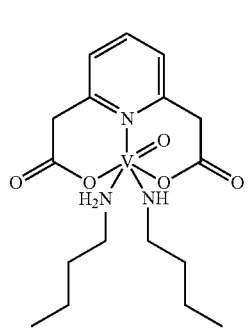

Complex 10

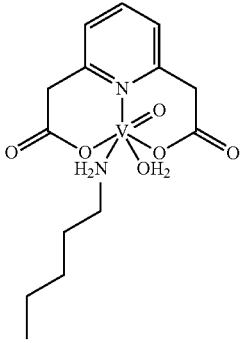

Complex 11
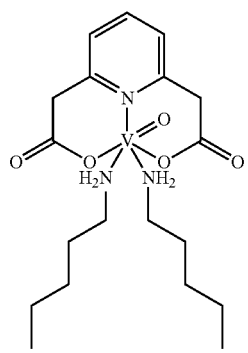
Complex 12
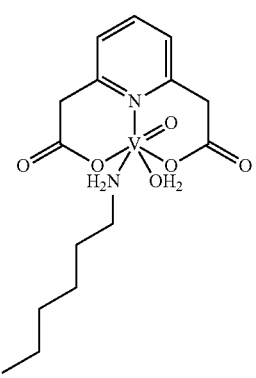
Complex 13
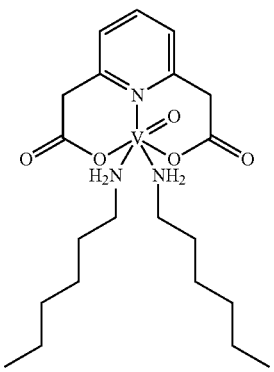
Complex 14
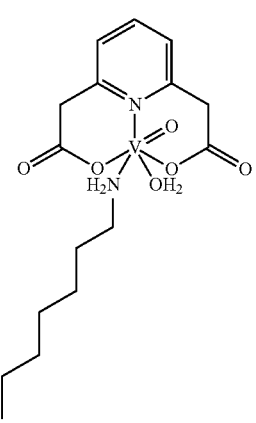
Complex 15
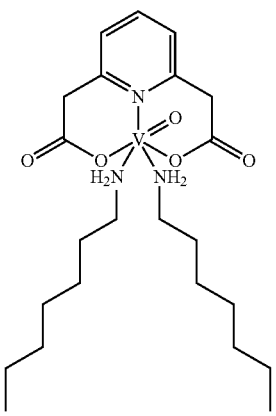
Complex 16
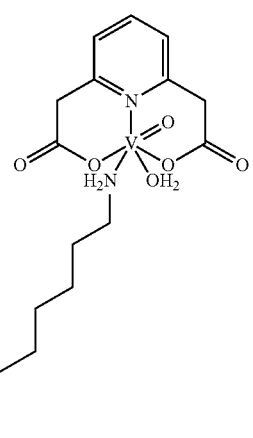
Complex 17
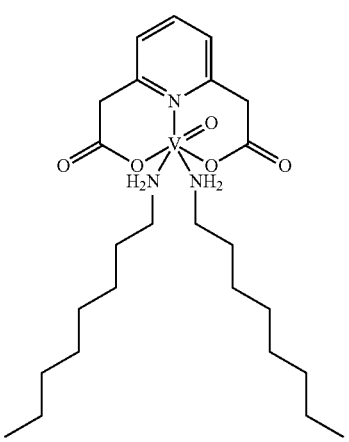

Complex 18
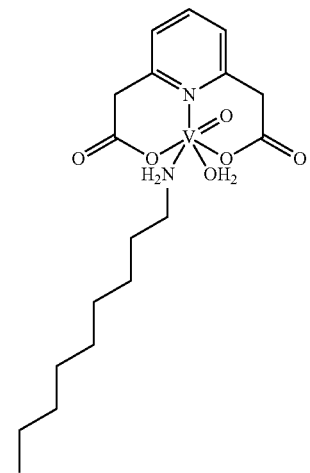
Complex 19
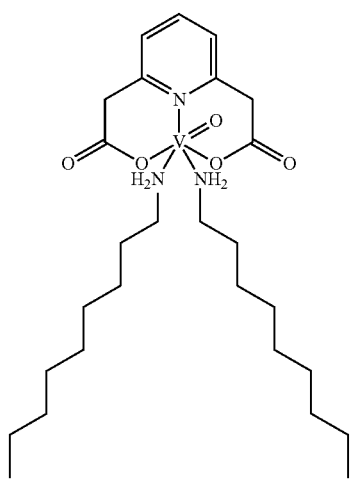
Complex 20
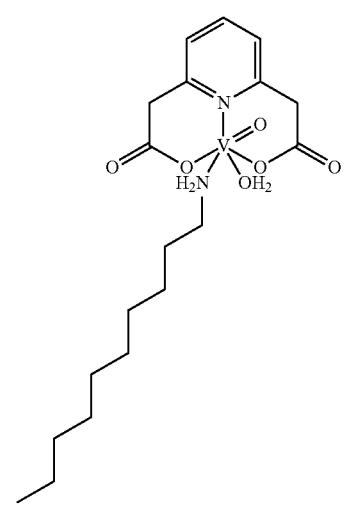
Complex 21
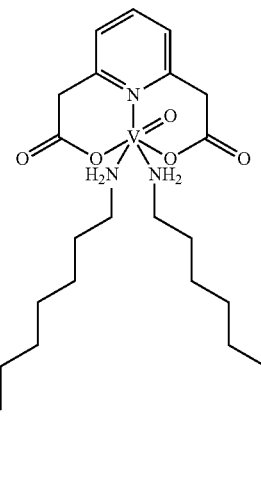
Complex 22
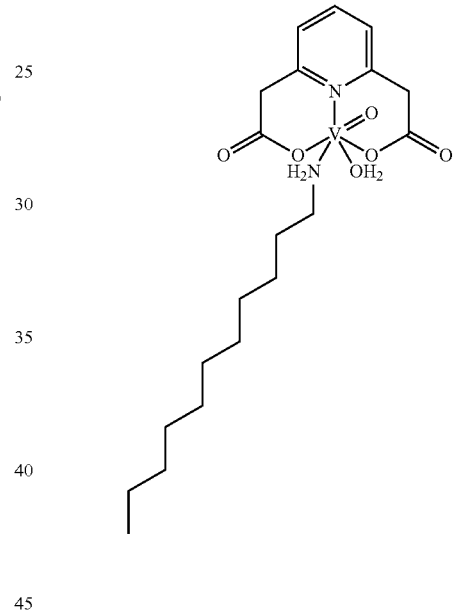
Complex 23
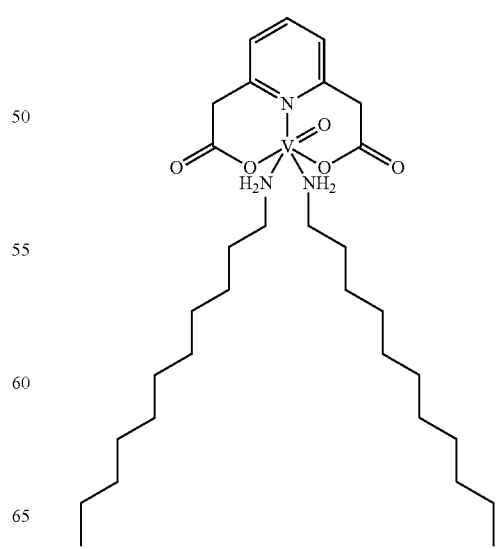

Complex 24
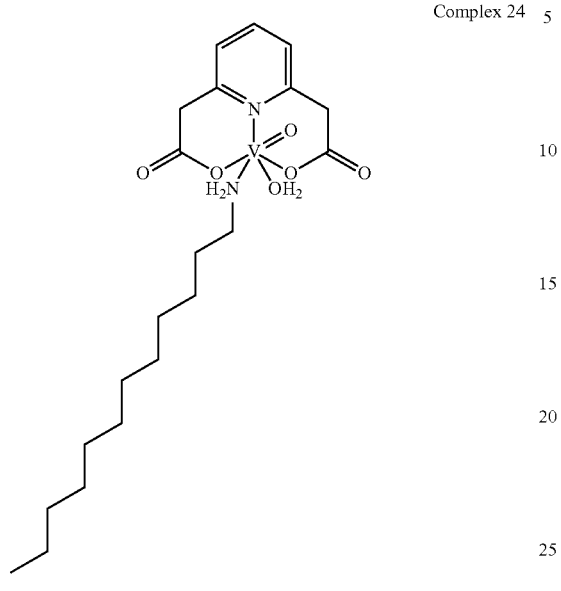
Complex 25
Complex 26
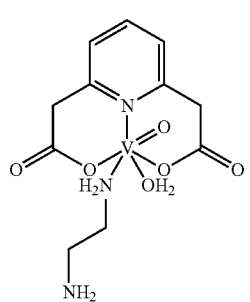
Complex 27
Complex 28
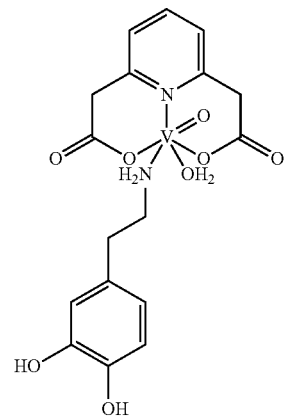
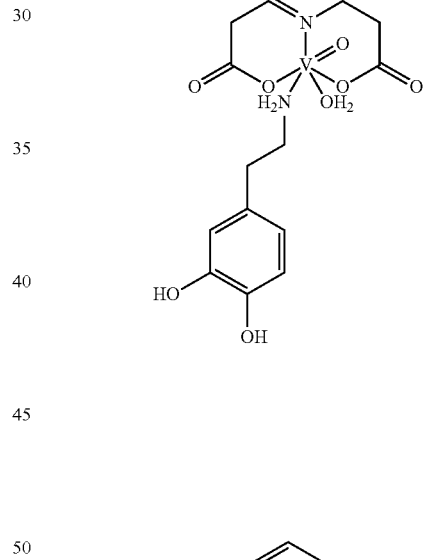
Complex 29
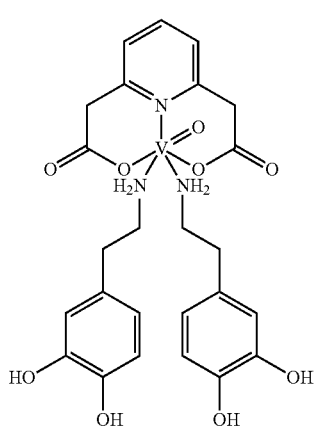
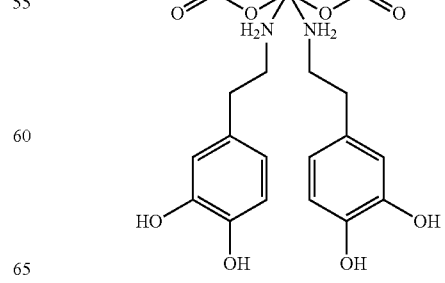

Synthesis of Formula 2
Formula 2 was generated using the following syntheses.

Reaction Scheme 2

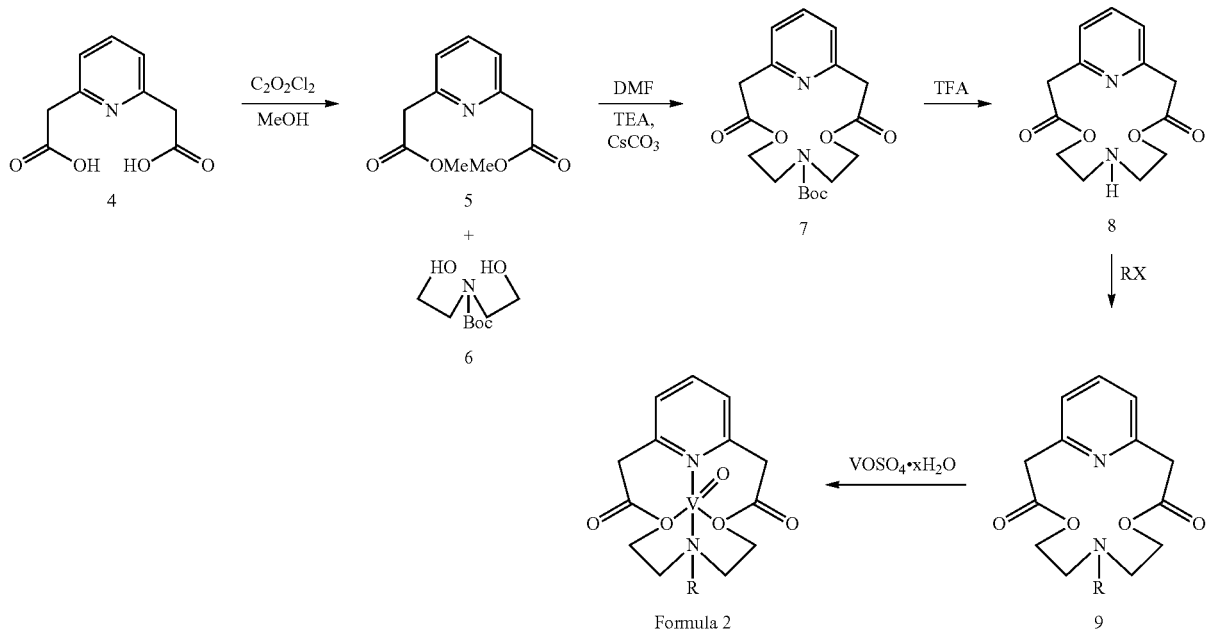

6-Methoxycarbonylmethyl-pyridin-2-yl)-acetic acid methyl ester (Methyl Ester Derivative of the Diacid) (5)

Compound 4 from Reaction Scheme 1 was reacted with oxalyl chloride in an ice bath, under inert conditions. After 1 and a half hours, the excess solvent was removed under pressure and a mixture of methanol, triethylamine and a catalytic amount of DABCO was added to the di-acylchloride under argon at 0° C. The reaction mixture was refluxed for two hours under argon and then brought to dryness by rotary evaporation. The crude product was purified via column purification using 40% PET/60% ethyl acetate as the solvent system. The product was fully characterized by IR, $^1$H and $^{13}$C NMR spectroscopy.

(0.11 g, 38.47%). IR: C=O 1700 cm$^{-1}$, C—O 1158 cm$^{-1}$, 1013 cm$^{-1}$. $^1$H NMR (600 Hz, CDCl$_3$): 7.75 (t, J=7.7, 1H). 7.20 (d, J=7.7, 2H), 3.85 (s, 4H), δ 3.65 (s, 6H), $^{13}$C NMR (600 Hz, CDCl$_3$): δ 171.1, 154.1, 137.2, 122.3, 52.1, 43.7.

Bis-(2-hydroxy-ethyl)-carbamic acid tert-butyl ester (6)

A 1000 ml RB flask equipped with a large Teflon coated magnetic stirrer was charged with 200 ml of saturated NaHCO$_3$ solution, 105.95 grams (1810 mmoles) NaCl, 400 ml of chloroform, 27.3 grams (259.7 mmol) of diethanolamine and 113.74 grams (521.4 mmol) of di-tert-butyl dicarbonate. The resulting mixture was heated to reflux (70° C.) for 20 hours and vigorously stirred. After cooling the reaction mixture was transferred to a 2000 ml separatory funnel. The bottom layer was collected and the top layer was further extracted with chloroform (3×50 ml). The organic layers were combined and washed with water (2×150 ml). Na$_2$SO$_4$ was added to the combined organic layers and the mixture was stirred for 15 minutes. After suction filtration, the solvent was removed to yield an oil. The crude (85.55 grams) was purified using a silica column. Solvent system: 2% MeOH in DCM. The product was eluted using 100% MeOH. A ninhydrin and methanol mixture was used to stain the TLC plates and spots became visible on heating.

(31.16 grams=[60.95%]). R$_f$(100% DCM)=0.33. $^1$H NMR (CDCl$_3$): δ 1.2 (s, 9H's), 3.1 (d, 4H's), 3.8 (d, 4H's). $^{13}$C NMR (CDCl$_3$): 27.48, 50.18, 59.82, 79.29, 155.46.

3,11-Dioxo-4,10-dioxa-7,17-diaza-bicyclo[11.3.1] heptadeca-1(16),13(17),14-triene-7-carboxylic acid tert-butyl ester (7)

0.1 grams (0.45 mmoles) of 6-Methoxycarbonylmethyl-pyridin-2-yl)-acetic acid methyl ester (5) was charged in a 100 ml 3-neck RB flask equipped with a magnetic stirrer and purged with Ar. 50 ml of Dry DMF was added to the to the flask followed by 0.3 g CsCO$_3$ (0.9 mmol) and 2 ml triethyl amine. The mixture was warmed to 80° C. with constant stirring. 0.1 g (0.45 mmol of Bis-(2-hydroxy-ethyl)-carbamic acid tert-butyl ester (6) in 5 ml DMF was then added dropwise via a Pressure equalizing funnel. The reaction mixture was allowed to stir for a further 12 hours at 80° C.

After the given reaction period, the solvent was removed from the reaction mixture under high vacuum and the crude was shaken in a mixture of 5 ml saline solution: 10 ml chloroform and then separated. The aqueous layer was then further extracted with 3×5 ml of chloroform and the organic layer was combined and dried over anhydrous Sodium Sulfate. Further purification of the product was done using column chromatography using 95% Dichloromethane: 5% Methanol.

The mixture of all reagents was added dropwise under argon and left to stir at room temperature for one hour. The solvent was removed by rotary evaporation and the residue was dissolved in 100 ml of water and 50 ml of DCM and left overnight in a 250 ml separator funnel. The bottom layer was collected and the top layer was further extracted with DCM (3×50 ml). The sample was brought to dryness by rotary evaporation. Mass of crude=5.06 g.

The crude was purified using a silica column. Solvent system: 5% MeOH in DCM. The first column yield 0.09 grams of product. The other fractions were combined and another column was done using 2% MeOH in DCM to give 0.06 grams of product.

(0.15 grams=0.0004 moles [3.19%]). $R_f$ (2% MeOH and DCM)=0.31. $^1$H NMR (CDCl$_3$): δ1.45 (s, 9H's), 3.6 (4H's, s, d), 3.8 (4H's, s), 4.3 (4H's, t), 7.1 (2H's, d), 7.6 (1H, t). $^{13}$C NMR (CDCl$_3$): 28.52, 43.88, 65.59, 80.27, 122.01, 137.69, 137.69, 155.18, 170.53.

Alternatively, Formula 2 can be generated using Reaction Scheme 3.

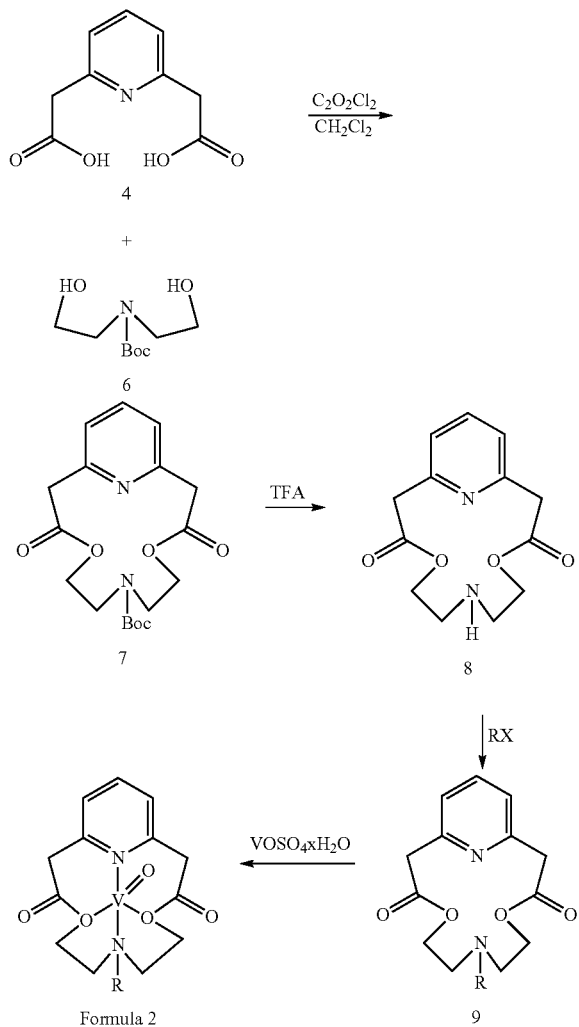

Reaction Scheme 3

3,11-Dioxo-4,10-dioxa-7,17-diaza-bicyclo[11.3.1] heptadeca-1(16),13(17),14-triene-7-carboxylic acid tert-butyl ester (7)

1.68 grams (8.6 mmoles) of 2,6 pyridine diacetic acid (4), DMF (1.5 ml) and distilled dichloromethane (DCM) (25 ml) was placed into a 500 ml, 3-neck RB flask equipped with a Teflon coated magnetic stirrer left under argon. 3.33 grams (26.3 mmoles) of oxalyl chloride (COCl)$_2$ was weighed into it 10 ml of DCM. The DCM/COCl$_2$ was added dropwise to 4 under argon at 0° C. then a further 15 ml of DCM was added to the reaction flask. The mixture was then left to stir at RT for one hour. Excess solvent was removed by vacuum distillation to yield the intermediate diacid dichloride. Under argon, 200 ml of DCM was added to the diacid dichloride. A solution of 2.47 grams (12 mmoles) the BOC-amine 6, Et$_3$N (3.3 grams, 29.6 mmoles) and DABCO (1 gram, 8.88 mmoles) in 50 ml of DCM was added dropwise to the diacid dichloride under argon and left to stir at 0° C. for one hour. The temperature was allowed to rise to RT and then and then allowed to stir for a further 12 h. The solvent was removed by rotary evaporation and the residue was dissolved in 30 ml of water and 20 ml of DCM and the organic layer was extracted. The aqueous layer was further extracted with 3×12 ml DCM. The sample was brought to dryness by rotary evaporation. The crude was purified by column chromatography. Solvent system: 2% MeOH in DCM.

(0.2 grams=0.55 mmoles [6.38%]). $R_f$ (2% MeOH and DCM)=0.31. $^1$H NMR (CDCl$_3$): δ1.45 (s, 9H's), 3.6 (4H's, s, d), 3.8 (4H's, s), 4.3 (4H's, t, J=3.4 Hz), 7.1 (2H's, d, 7.1), 7.6 (1H, t, J=7.6). $^{13}$C NMR (CDCl$_3$): 28.52, 43.88, 65.59, 80.27, 122.01, 137.69, 137.69, 155.18, 170.53. IR (cm$^{-1}$): 1735 C=O stretch, 1283 and 1245 C—O stretches.

4,10-Dioxa-7,17-diaza-bicyclo [11.3.1]heptadeca-1 (16),13(17),14-triene-3,11-dione (8)

0.2 grams (0.55 mmol) of 3,11-Dioxo-4,10-dioxa-7,17-diaza-bicyclo[11.3.1]heptadeca-1(16), 13(17), 14-triene-7-carboxylic acid tert-butyl ester was dissolved in 4.5 ml of DCM. TFA (1 ml) was added to the solution at 0° C. The ice was left to thaw to RT and left to stir for 3.5 hours. The solvents were removed by rotary evaporation and the residue was dissolved in DCM (5 ml). The mixture was cooled to 0° C. and neutralized using saturated NaHCO$_3$ solution. The mixture is allowed to warm to RT and stirred for one hour. The organic layer is extracted and reduced by rotary evaporation. The crude was purified by column chromatography. Solvent system: 7% MeOH in DCM.

(0.09 grams=0.34 mmoles [78%]). $R_f$ (7% MeOH and DCM)=0.375. $^1$H NMR (CDCl$_3$): δ 2.69 (4H's, t, J=4.69), 3.78 (4H's, s), 4.19 (4H's, t, J=4.91 Hz), 7.08 (2H's, d, J=7.74), 7.57 (1H, t, J=7.85). $^{13}$C NMR (CDCl$_3$): 44.87, 46.89, 63.18, 122.38, 137.21, 154.60, 169.57. IR (cm$^{-1}$): 1727 C=O stretch, 1264 and 1132 C—O stretches.

Functionalized Derivatives (9)

0.1 g, (3.78×10$^{-4}$ mol) macrocycle intermediate 8 and an equivalent number of mols of the corresponding halogenated-pendant group were charged in a 50 ml RB flask. 0.1 g (7.57×10$^{-4}$ mol) K$_2$CO$_3$, 0.11 ml (7.57×10$^{-4}$ mol) trimethylamine and 25 ml dry DMF were then added to the reaction flask. The mixture was left to stir for 6 hours at 80° C. under Argon, after which it was filtered through celite, and the filtrate reduced to dryness under reduced pressure and temperature. The residue was taken up in 20 ml saturated saline solution and then extracted with 3×10 ml dichloromethane. The organic extracts were combined and dried over sodium sulfate (anhydrous) filtered and the filtrate reduced to dryness using rotary evaporation to obtain Compound 9. Further purification was achieved via column chromatography using 2% MeOH in DCM.

Formula 2 is readily obtained by a simple one-to-one stoichiometric complexation reaction.

Vanadyl Complexes 30-50
Complexes 30-50 were obtained using the same procedure as outlined above for Complexes 1-29, but using the precursor ligands 8 or 9, instead of 2,6-pyridine diacetic acid (4).
Complex 30
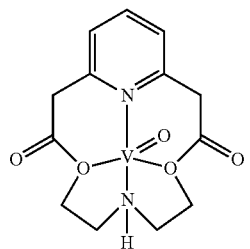
Complex 31
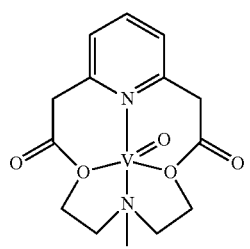
Complex 32
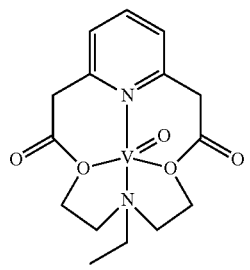
Complex 33
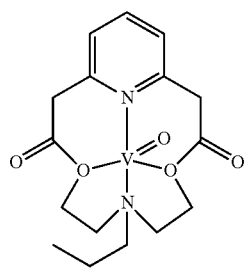
Complex 34
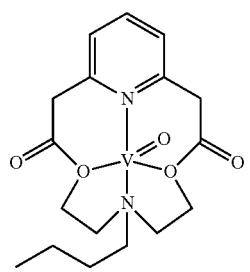
-continued
Complex 35
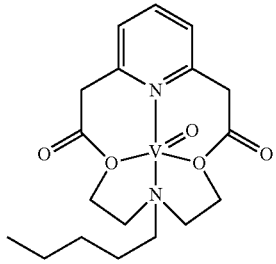
Complex 36
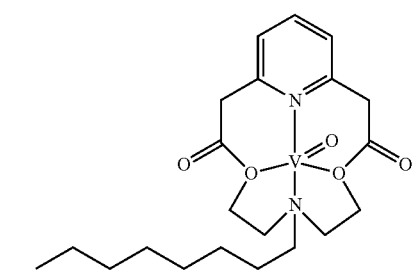
Complex 37
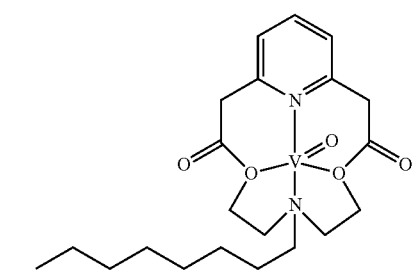
Complex 38
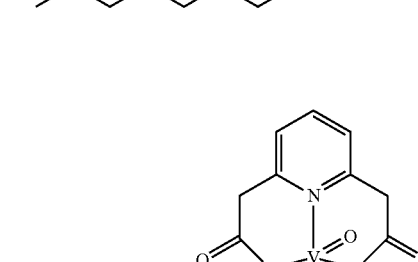
Complex 39
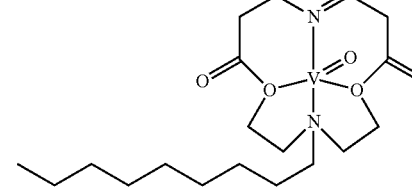

Complex 40
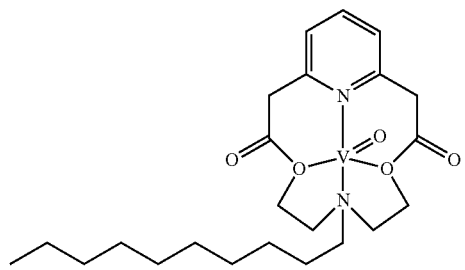
Complex 41
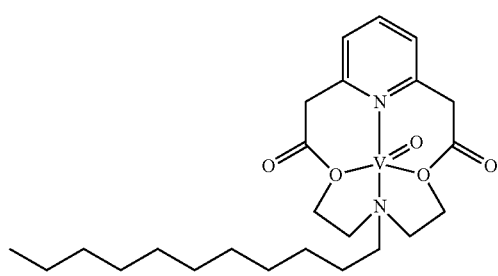
Complex 42
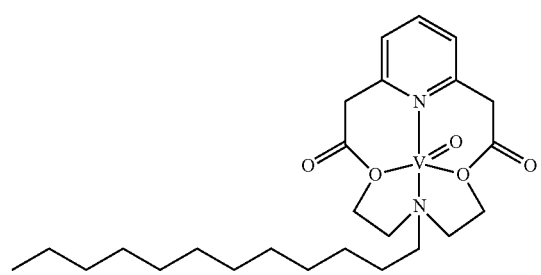
Complex 43
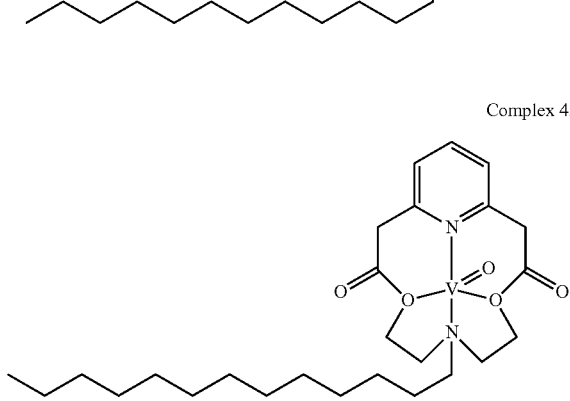
Complex 44
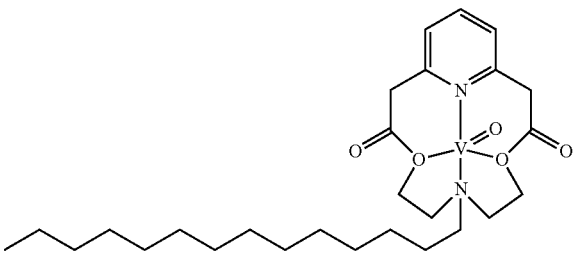
Complex 45
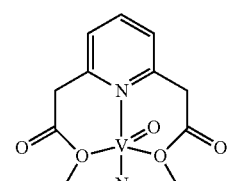
Complex 46
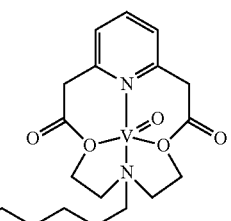
Complex 47
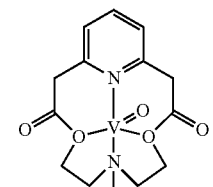
Complex 48
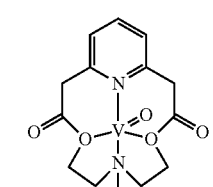
Complex 49
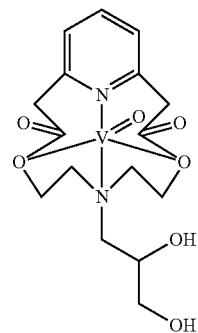

Complex 50

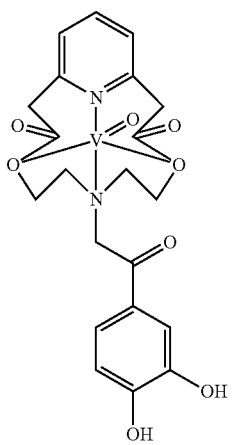

Synthesis of Formula 3
Formula 3 was generated using the following syntheses.

Reaction Scheme 4

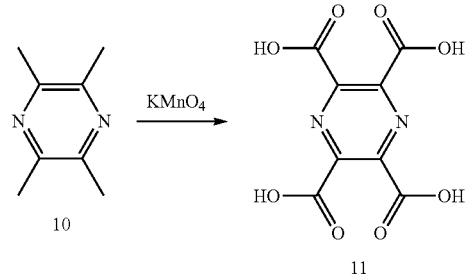

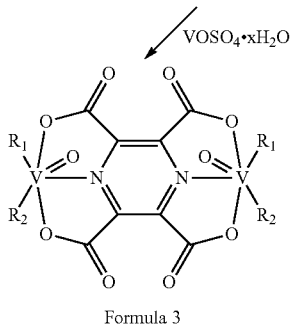

Formula 3

Preparation of 2,3,5,6-pyrazinetetracarboxylic acid (11)

Tetramethylpyrazine (10) and sodium hydroxide are suspended in hot deionized water. Hot potassium permanganate ($KMnO_4$) solution is then slowly added after which the mixture is stirred for a further 2 hours at room temperature prior to refluxing for 24 hours. The solution is cooled to room temperature using an ice bath and ethanol is then added to the mixture to destroy any excess $KMnO_4$. The volume of solution is reduced and then cooled to allow crystallization of the product over a period of 24 hours.

Vanadyl Complex 51

Complex 51 was obtained using the same procedure as outlined above for Complexes 1-29, but using the precursor ligand 11, instead of 2,6-pyridine diacetic acid (4).

Complexes 52-67 were obtained using the same procedure as outlined above for the synthesis of Complexes 2-29, but using the precursor Complex 51 instead of Complex 1.

Complex 51

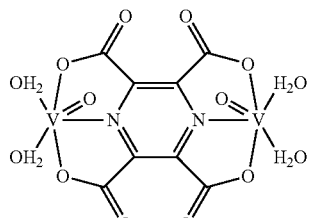

Complex 52

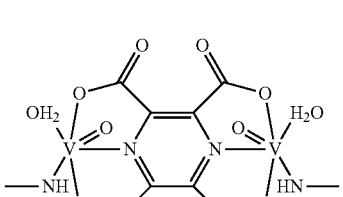

Complex 53

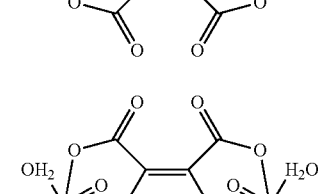

Complex 54

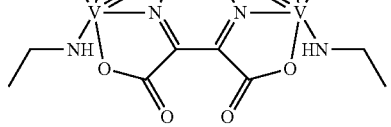

Complex 55

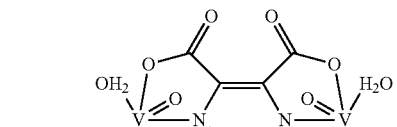

Complex 56

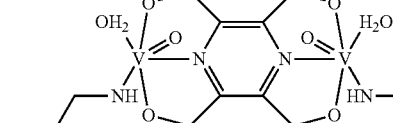

Complex 57

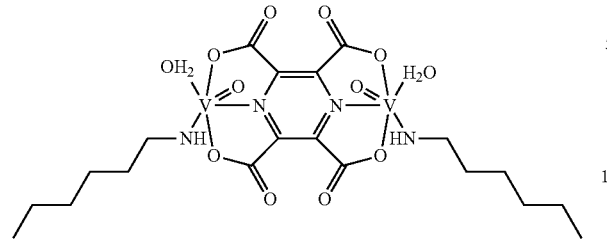

Complex 58

Complex 59

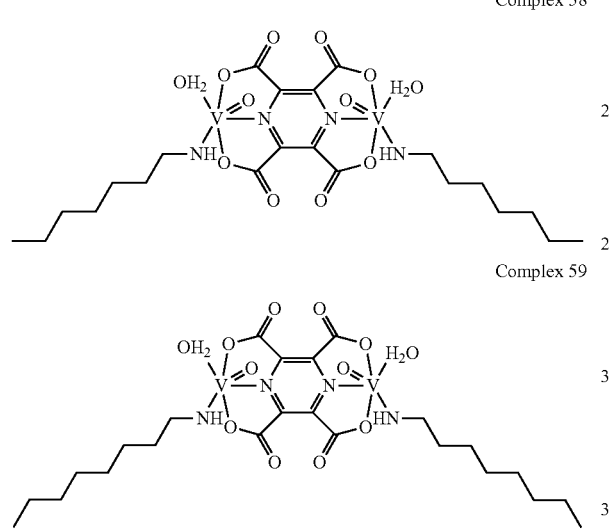

Complex 60

Complex 61

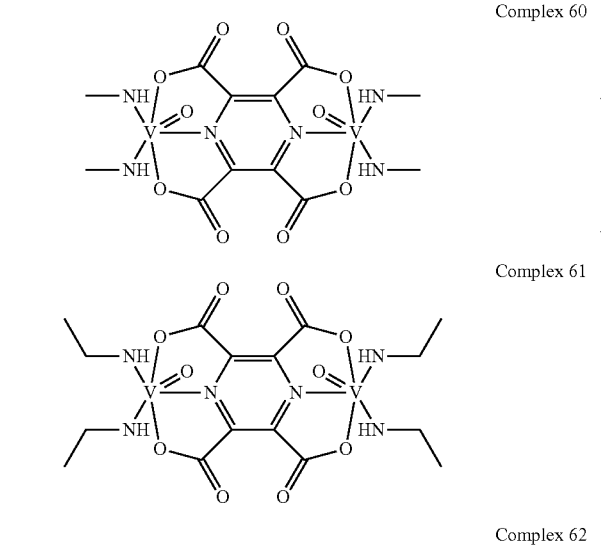

Complex 62

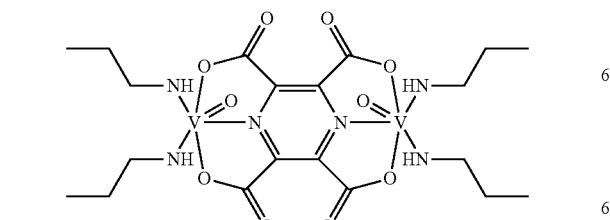

Complex 63

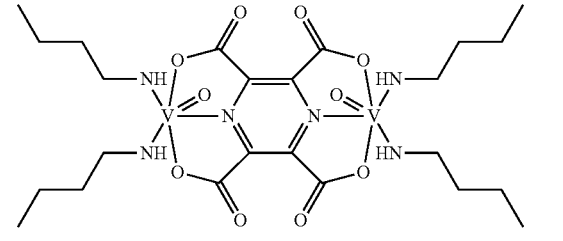

Complex 64

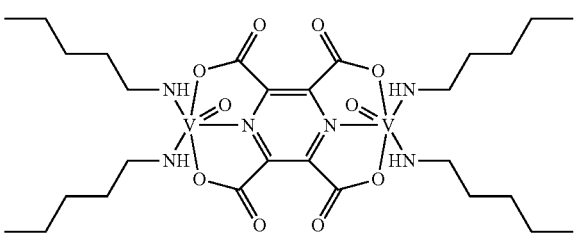

Complex 65

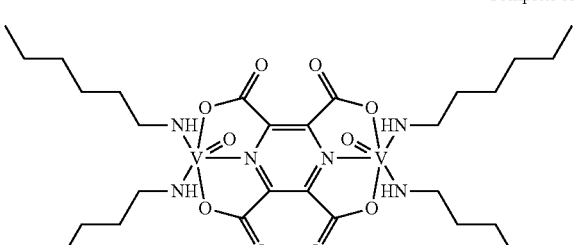

Complex 66

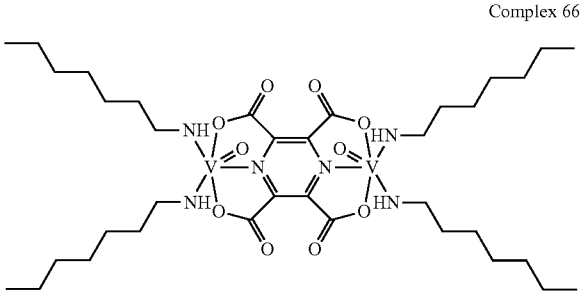

Complex 67

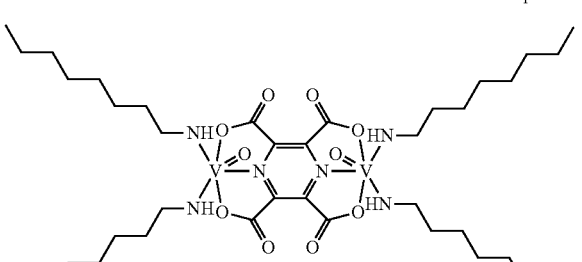

The instant disclosure also provides a composition comprising at least one compound and/or at least one pharmaceutically acceptable salt described herein, and at least one pharmaceutically acceptable carrier.

Before use, the at least one compound and/or at least one pharmaceutically acceptable salt described herein, can be purified by column chromatography, high performance liquid chromatography, crystallization, or other suitable methods.

A composition comprising at least one compound and/or at least one pharmaceutically acceptable salt described herein, can be administered in various known manners, such as orally, parenterally, transdermally, by inhalation spray, or via an implanted reservoir. The term "parenteral" as used herein includes subcutaneous, intracutaneous, intravenous, intraperitoneal, intramuscular, intraarticular, intramuscular, intravenous, intra-arterial, intrasynovial, intrasternal, intrathecal, intralesional and intracranial injection or infusion techniques.

An oral composition can be any orally acceptable dosage form including, but not limited to, tablets, capsules, emulsions, aqueous suspensions, dispersions, hydrogels, and solutions. Commonly used carriers for tablets include lactose and corn starch. Lubricating agents, such as magnesium stearate, are also typically added to tablets. For oral administration in a capsule form, useful diluents include lactose and dried corn starch.

When aqueous suspensions, hydrogels, or emulsions are administered orally, the active ingredient can be loaded in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable Intermediate can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution.

In addition, sterile, fixed oils are conventionally employed as a solvent or suspending medium (e.g., synthetic mono- or di-glycerides). Fatty acids, such as oleic acid and its glyceride derivatives are useful in the intermediate of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A pharmaceutically acceptable carrier refers to a carrier that is compatible with active ingredients of the composition (and in some embodiments, capable of stabilizing the active ingredients) and not deleterious to the subject to be treated. For example, solubilizing agents, such as cyclodextrins (which form specific, more soluble complexes with the at least one compound and/or at least one pharmaceutically acceptable salt described herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10.

Nanoparticles can also act as carriers for the active ingredients of the composition and in some embodiments, are also capable of stabilizing the active ingredients. In addition, nanoparticles are not deleterious to the subject to be treated. For example, suitable nanoparticles include mesoporous silica nanoparticles (see, for example, Zhao et al. (2009) *J Am Chem Soc* 131(24): 8398-8400), including but not limited to MCM-41 nanoparticles, hydrogels (see, for example, Mura et al. (2013) *Nat Mater* 12:991-1003), glucose-responsive micelles (see, for example, Wang et al. (2009) *Langmuir* 25(21): 12522-12528), and polymersomes (see, for example, Kim et al. (2012) *ACS Macro Lett* 1:1194-1198). The pH of the stomach environment is typically about pH 1.7, whereas the duodenum is about pH 6, the small intestine is about pH 6-7.4, the caecum about pH 5.7, and the rectum is about pH 6.7. Blood has a pH of about 7.4. Consequently, in order to be protected from degradation in the stomach and to allow effective release in the intestinal tract, nanoparticles loaded with a drug must contain some type of protective barrier. Suitable mesoporous silica nanoparticles include those (a) functionalized with a variety of moieties (e.g. boronic acid, glucosamine, etc.), (b) pore-neck blocked with small nanoparticles (e.g. $Fe_3O_4$ NP, AuNPs, etc.), (c) pore-neck blocked with biomolecules (e.g. enzymes, protein, etc.), and (d) surface capped with biopolymers (e.g. chitosan, dextran, hyaluronic acid, etc.).

Suitable in vitro assays can be used to preliminarily evaluate the efficacy of the at least one compound and/or at least one pharmaceutically acceptable salt described herein, in controlling DM. The at least one compound and/or at least one pharmaceutically acceptable salt described herein, can further be examined for efficacy in treating DM by in vivo assays. For example, the compounds described herein, and/or the pharmaceutically acceptable salts thereof, can be administered to an animal (e.g., a mouse or rat model) having DM and its therapeutic effects can be accessed.

Based on the results, an appropriate dosage range and administration route for animals, such as humans, can also be determined.

In some embodiments, other drugs known to treat DM can be co-administered with the compounds disclosed. Such drugs include sulfonylureas (e.g. tolbutamide, glimepiride, glimepiride-pioglitazone, glimepiride-rosiglitazone, gliclazide, glipizide, glipizide-metformin, chlorpropamide, tolazamide, etc.), insulin (including short-acting, rapid-acting (e.g.insulin aspart, insulin glulisine, insulin lispro, etc.), intermediate-acting (e.g. insulin isophane, etc.), long-acting (e.g. insulin degludec, insulin determir, insulin glargine, etc), and combination insulins), amylinomimetic drugs (e.g. pramlintide, etc.), alpha-glucosidase inhibitors (e.g. acarbose, miglitol, etc.), biguanides (e.g. metformin, etc.), biguanide combinations (e.g. metformin-alogliptin, metformin-canagliflozin, metformin-dapagliflozin, metformin-empagliflozin, metformin-glipizide, metformin-glyburide, metformin-linagliptin, metformin-pioglitazone, metformin-repaglinide, metformin-rosiglitazone, metformin-saxagliptin, metformin-sitagliptin, etc.), dopamine agonists (e.g. bromocriptine, etc.), DPP-4 inhibitors (e.g. alogliptin, alogliptin-metaformin, alogliptin-pioglitazone, linagliptin, lnagliptin-empagliflolin, linagliptin-metformin, saxagliptin, saxagliptin-metaformin, sitagliptin, sitagliptin-metofirmin, stiaglipin and simvastatin, etc.), glucagon-like peptides/incretin mimetics (e.g. albiglutide, dulaglutide, exenatide, exenatide extended-release, liraglutide, etc.), meglitinides (e.g. ntaglinide, repaglinide, repagline-metformin, etc.), sodium glucose transporter (SGLT) 2 inhibitors (e.g. dapaglifolozin, dapagliflozin-metformin, canagliflozin, canagliflozin-metformin, empagliflozin, empagliflozin-linagliptin, empagliflozin-metformin, etc.), thiazolidinediones (e.g. rosiglitazone, rosiglitazone-glimepiride, rosiglitazone-metformin, pioglitazone, pioitazone-alogliptin, pioglitazone-glimepiride pioglitazone-metformin, rosiglitazone maleate, etc.), and cyclic adenosine monophosphate (cAMP).

Example 1

Streptozotocin (STZ; 2-deoxy-2-(3-methyl-3-nitrosoureido)-D-glucopyranose), a diabetogenic agent having the ability to induce pancreatic β-cell toxicity, is one of the chemicals used worldwide to induce diabetes in a simple and convenient method.

Adult albino mice, *Mus musculus*, three months old, weighing 30±5 g were procured from Sri Raghavendra Enterprises, Bangalore and acclimatized to laboratory conditions (12:12 hr dark/light, 25±2° C.) for one week. During acclimatization and thereafter, mice were maintained on standard rodent pellet and tap water ad libitum in accordance with ethical guidelines for animal care and experimentation.

Six (6) groups with six mice each were used. Group I consisted of control animals and Groups II-VI animals were made diabetic by single dose intraperitoneal injection of STZ (60 mg/kgbw in 0.1 mol/l citrate buffer (pH 4.5), in a volume of 1 ml/kgbw) and induced diabetic/hyperglycemic state (<180 mg/dl blood glucose levels) confirmed. Group II became the positive control. Groups III-VI animals were subjected to different doses of Sephadex purified Complex-I. Group III was given a first intraperitoneal injection of 50 mg/kgbw of Complex 1 dissolved in 0.9% saline. Similarly, Groups IV, V and VI were given first doses of 150, 250, 300 mg/kgbw intraperitoneally. On the fifth day after the first administration, blood was collected by tail pricking and blood glucose levels measured using an ACCU-CHECK® glucometer on a daily basis. Subsequently each group was given its respective second and subsequent doses through intraperitoneal injection.

Among the different doses of Complex 1 administered, 250 mg/kgbw at multiple doses showed a stable and sustainable blood glucose level throughout the study, while the other doses showed an irregularity in maintaining the reduced levels. In comparison to daily insulin administration as seen in diabetics, Complex 1 showed an advantage of attenuating blood glucose levels via administration once every 5 days instead of daily insulin injections. Conclusively, in the absence of insulin in STZ induced diabetic mice, Complex 1 at a dose of 250 mg/kgbw reduced the hyperglycemic condition in a steady state for a period of 30 days (data not shown).

Example 2

In Vivo Effect of Intraperitoneal Administration of Complex 1

Healthy adult male albino *Rattus norvegicus* Wistar rats, weighing 170-200 g were procured from Sri Raghavendra Enterprises, Bangalore, Karnataka, India. Studies were conducted in accordance with the guidance for the care and standard experimental animal ethical protocols. Animals were acclimated for a week, maintained at room temperature of 25±2° C. with 12-h dark-light cycle and given tap water and a standard rodent pellet diet ad libitum.

Six (6) groups with six rats each were used. Group I consisted of control animals and diabetes was induced in 12 hour fasted rats in Groups II-VI by a single intraperitoneal 60 mg/kgbw dose of STZ dissolved in freshly prepared 0.1 mol/L citrate buffer (pH 4.5). Blood samples obtained by sequential snipping of the tail and blood glucose levels measured using an ACCU-CHECK® glucometer on a daily basis. Rats exhibiting >180 mg/dl moderate hyperglycemia were used. Animals were tested until they were observed to be diabetic; i.e. having an induced diabetic/hyperglycemic state (206 mg/dl to 235 mg/dl blood glucose levels). Group II became the positive control.

Complex 1 prepared and purified without Sephadex according to paragraphs [107] and [108] was dissolved in 0.1 ml phosphate buffered saline (PBS) and administered intraperitoneally to STZ-induced diabetic rats. The dose-response of the drug was monitored for a period of 30 and 90 days using differential grades of drug at doses of 1, 10, 25, 50, 75, and 100 mg/kgbw administered once every five days. On the fifth day after the first administration, blood was collected and blood glucose levels measured using an ACCU-CHECK® glucometer. Subsequently each group was given its respective second and subsequent doses through intraperitoneal injection.

The following values were determined spectrophotometrically: (a) daily blood glucose levels (via Accu-check glucometer kit, Roche Diagnostics India); (b) hepatic glycogen (see Seifter et al., (1950) *Arch Biochem* 25(1):191-200); (c) glycosylated hemoglobin (see Sudhakar and Pattabiraman (1981) *Clin Chim Acta* 109:267-274); (d) blood urea nitrogen (BUN); (e) serum creatinine (see Hare (1950) *Proc Soc Exp Biol Med* 74:148-151); and (f) hepatic enzymes (AST, ALT) (see Reitman and Frankel (1957) *Am J Clin Pathol* 28:56-63).

Biostatistical analysis was conducted using SPSS 20.0 software. Analysis of variance (one-way ANOVA) was performed with the Tukey HSD post hoc test.

Figure 10A:
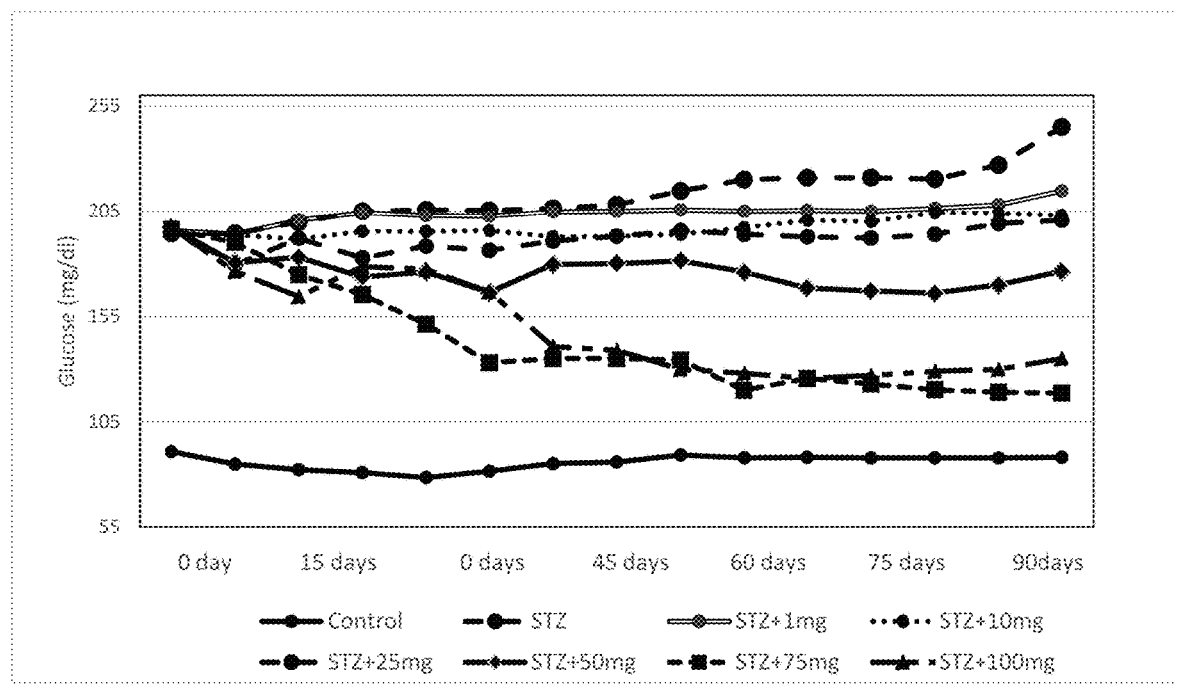
FIGS. 10A-10B: Dose-response of Complex 1 on blood glucose over a period of 30 days and 90 days at doses of 1, 10, 25, 50, 75, and 100 mg/kgbw administered intraperitoneally once every five days to STZ-induced diabetic mice.
Figure 10B:
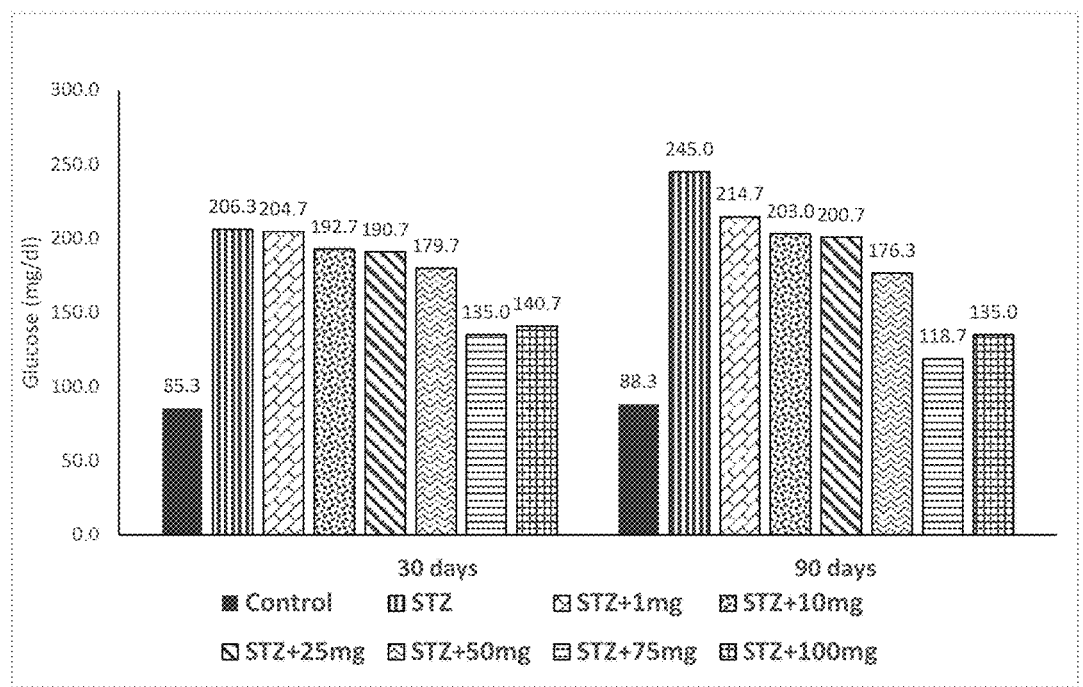
Figure 24:
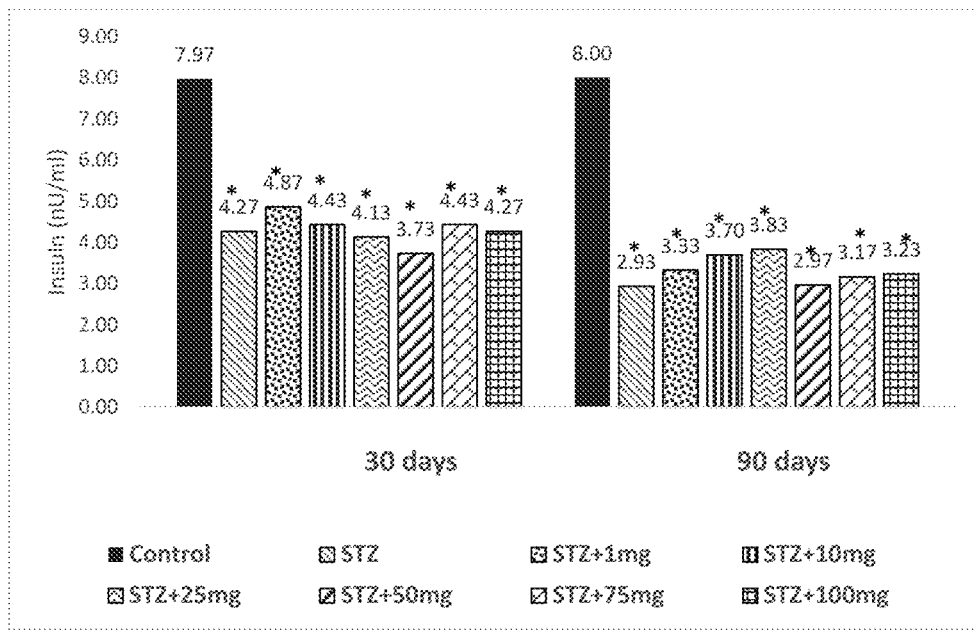
FIG. 24: Insulin response to Complex 1 over a period of 30 days and 90 at doses of 1, 10, 25, 50, 75, and 100 mg/kgbw administered intraperitoneally once every five days to STZ-induced diabetic mice. $P<0.05$ analysis via One-way analysis of variance (ANOVA) using Tukey HSD post hoc.

A Complex 1 dose of 75 mg/kgbw was found to be effective in suppressing the hyperglycemic state (135 mg/dl) after 30 days while three months supplementation of Complex 1 at 75 mg/kgbw was found to pronounce a significant (P<0.05) recovery in lowering the blood glucose levels (118.7 mg/dl) in diabetic mice (FIGS. 10A-10B) as well as significantly reducing insulin levels as compared to the control (FIG. 24).

Figure 11:
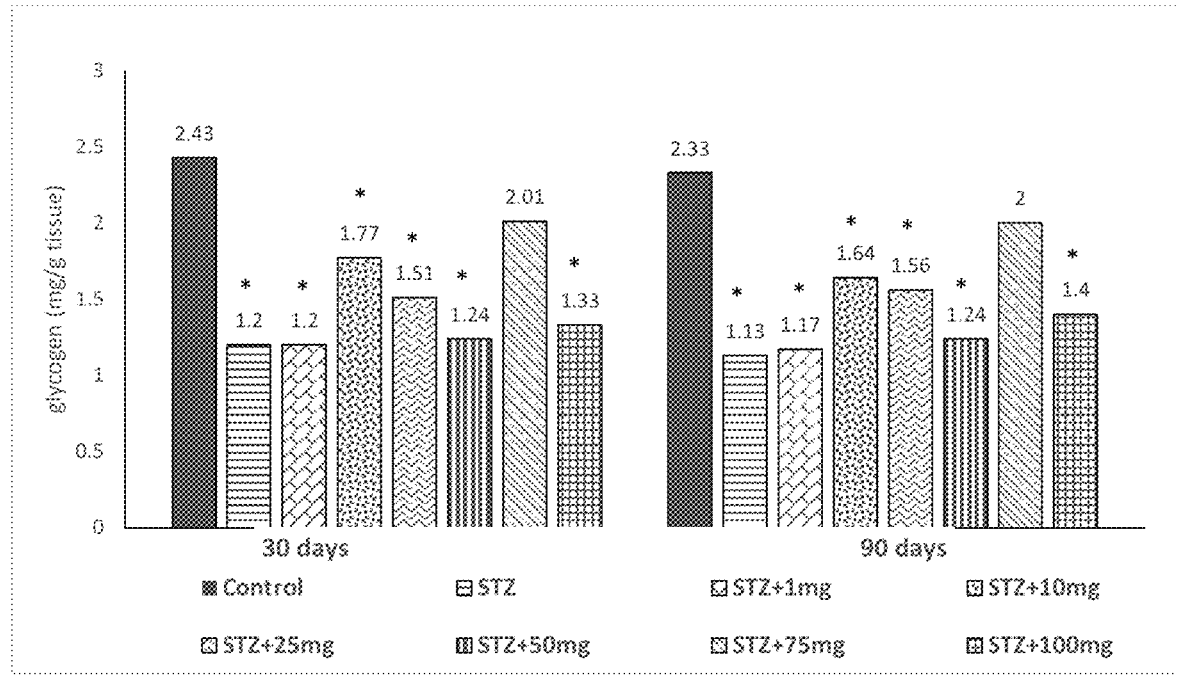
FIG. 11: Glycogen response to Complex 1 over a period of 30 days and 90 days at doses of 1, 10, 25, 50, 75, and 100 mg/kgbw administered intraperitoneally once every five days to STZ-induced diabetic mice. $P<0.05$ analysis via One-way analysis of variance (ANOVA) using Tukey HSD post hoc.
Figure 12:
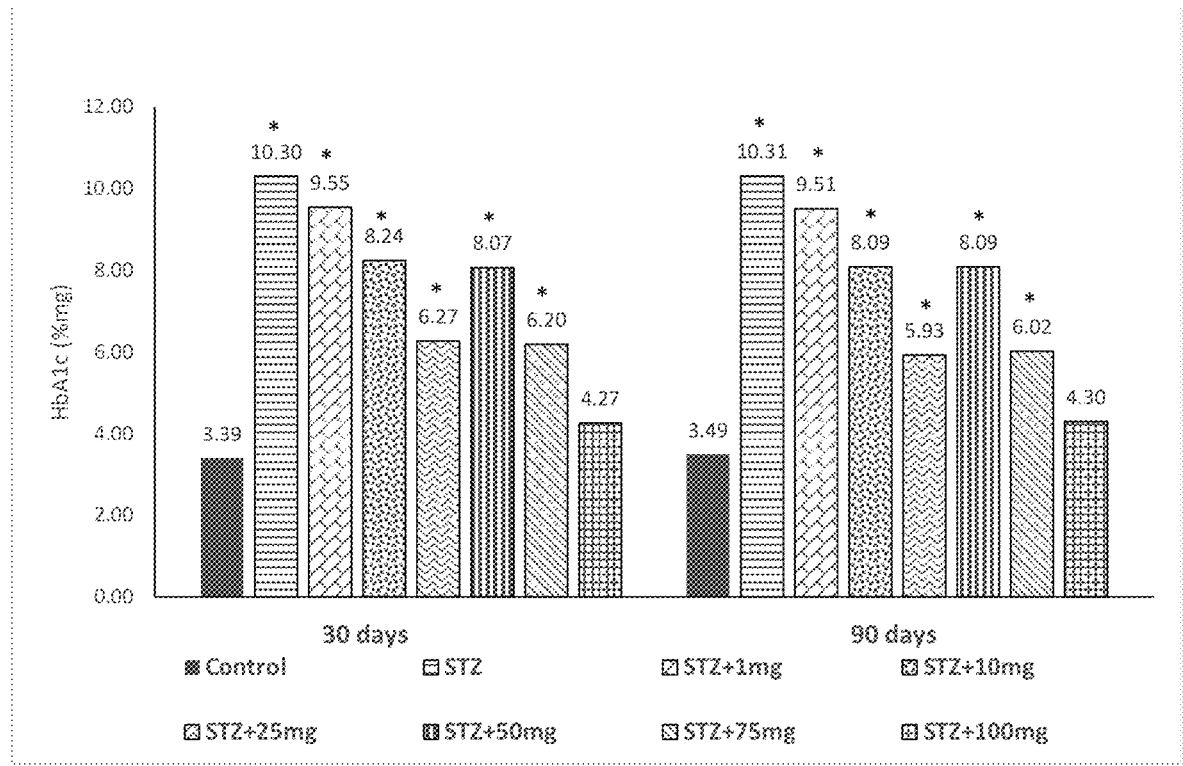
FIG. 12: Hemoglobin A1c (HbA1c) response to Complex 1 over a period of 30 days and 90 days at doses of 1, 10, 25, 50, 75, and 100 mg/kgbw administered intraperitoneally once every five days to STZ-induced diabetic rats. $P<0.05$ analysis via One-way analysis of variance (ANOVA) using Tukey HSD post hoc.
Figure 13:
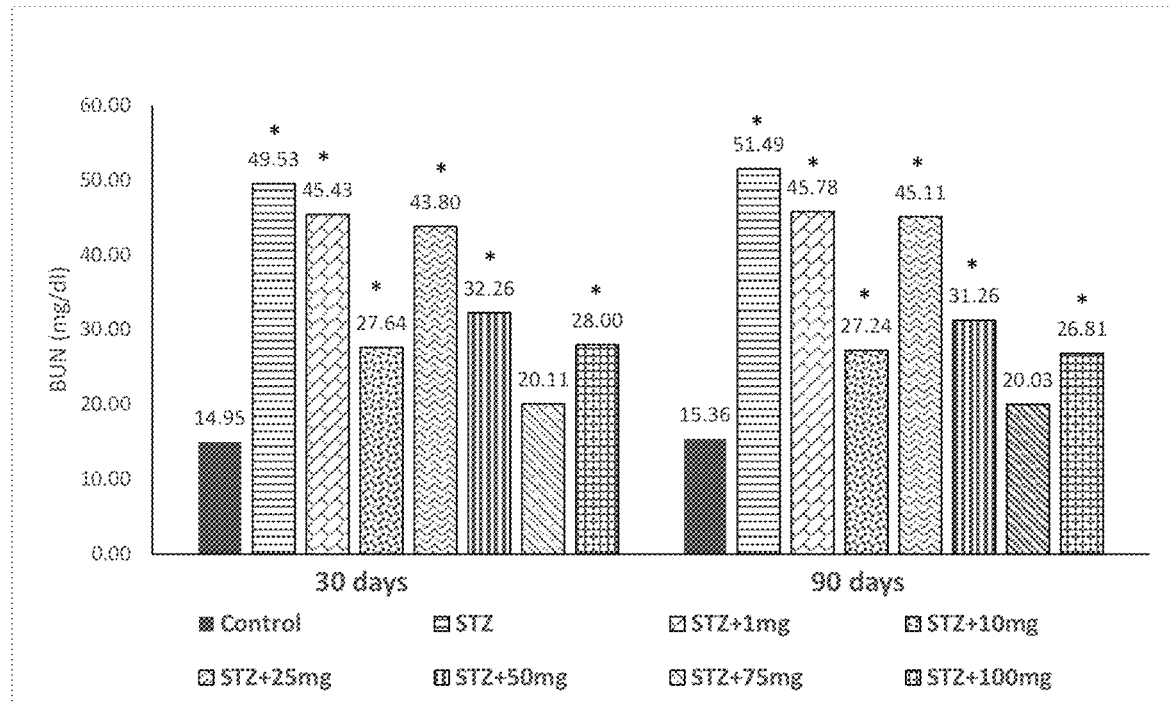
FIG. 13: Blood urea nitrogen (BUN) response to Complex 1 over a period of 30 days and 90 days at doses of 1, 10, 25, 50, 75, and 100 mg/kgbw administered intraperitoneally once every five days to STZ-induced diabetic rats. $P<0.05$ analysis via One-way analysis of variance (ANOVA) using Tukey HSD post hoc.
Figure 14:
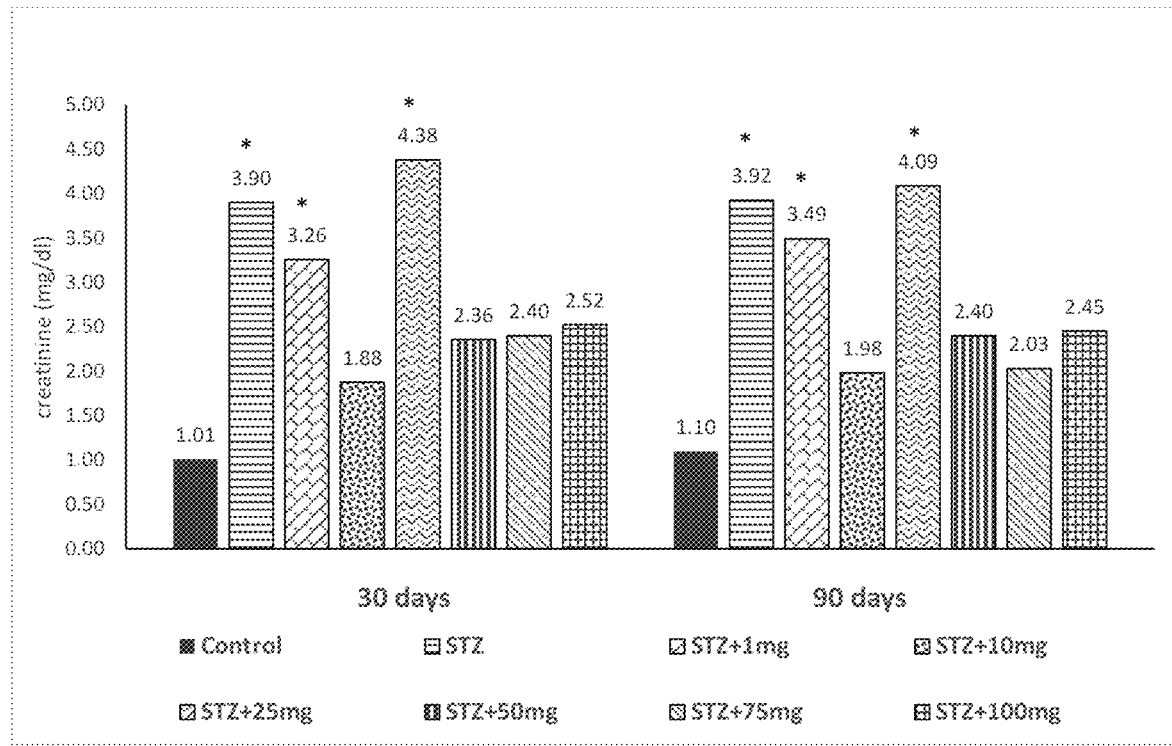
FIG. 14: Creatinine response to Complex 1 over a period of 30 days and 90 days at doses of 1, 10, 25, 50, 75, and 100 mg/kgbw administered intraperitoneally once every five days to STZ-induced diabetic rats. $P<0.05$ analysis via One-way analysis of variance (ANOVA) using Tukey HSD post hoc.
Figure 15:
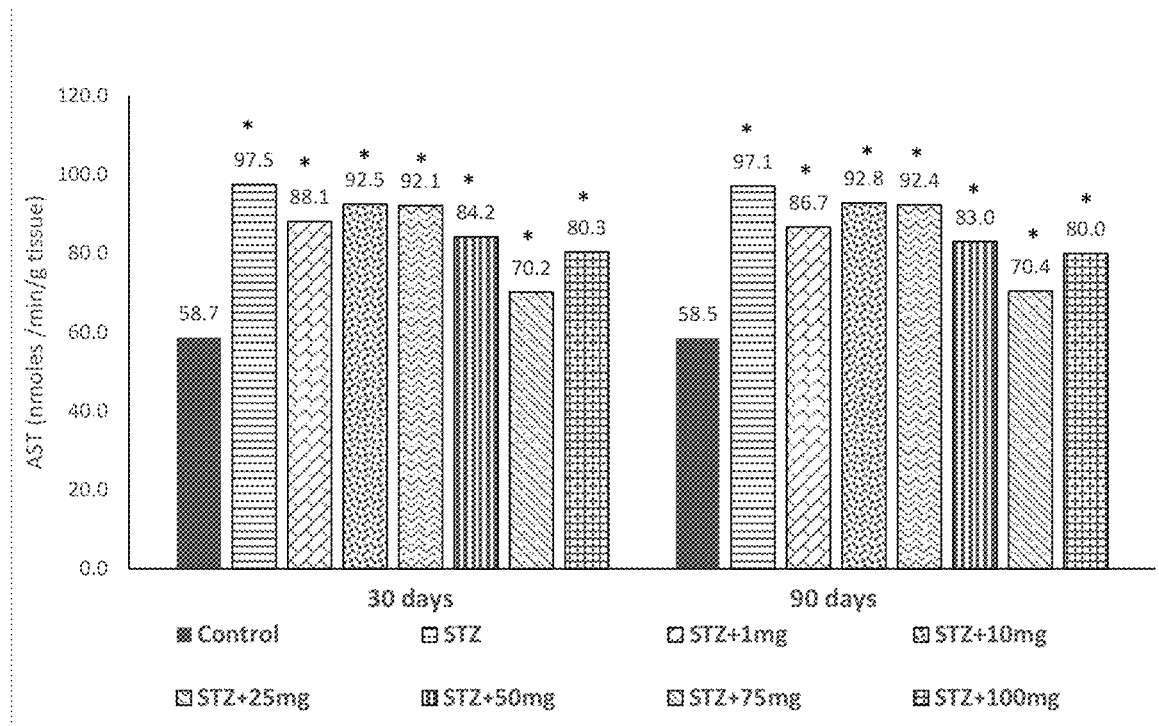
FIG. 15: Aspartate aminotransferase (AST) response to Complex 1 over a period of 30 days and 90 days at doses of 1, 10, 25, 50, 75, and 100 mg/kgbw administered intraperitoneally once every five days to STZ-induced diabetic rats. $P<0.05$ analysis via One-way analysis of variance (ANOVA) using Tukey HSD post hoc.
Figure 16:
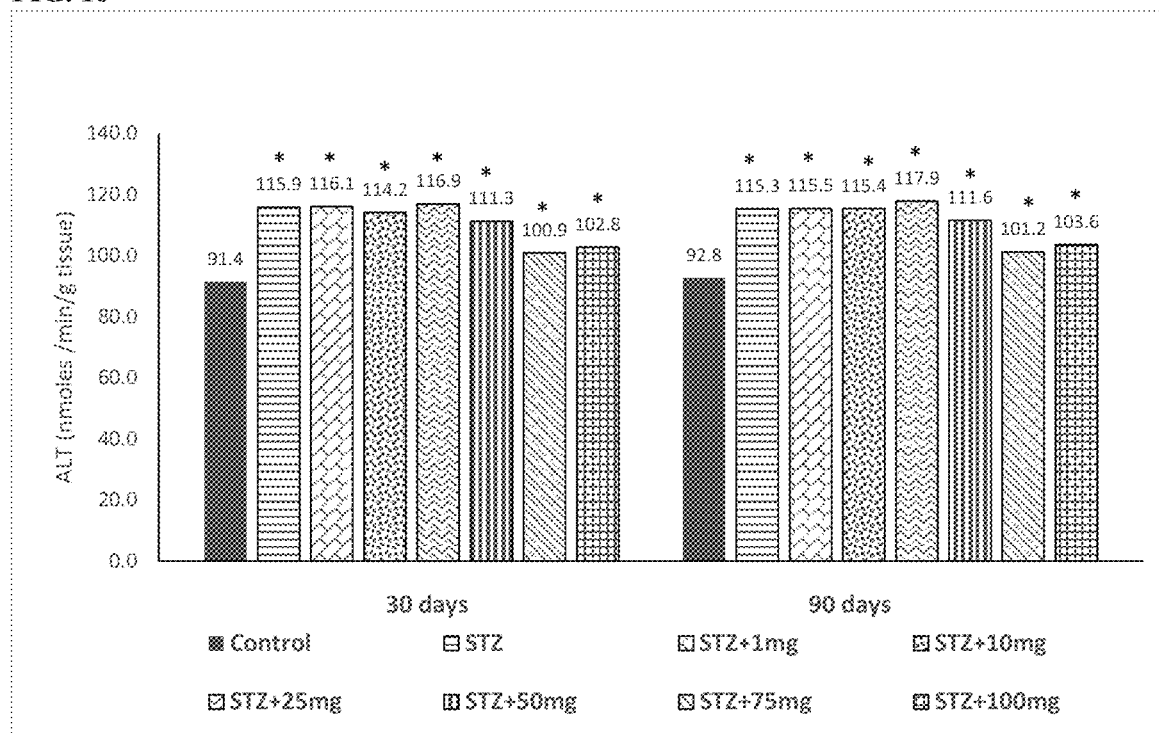
FIG. 16: Alanine aminotransferase (ALT) response to Complex 1 over a period of 30 days and 90 days at doses of 1, 10, 25, 50, 75, and 100 mg/kgbw administered intraperitoneally once every five days to STZ-induced diabetic rats $P<0.05$ analysis via One-way analysis of variance (ANOVA) using Tukey HSD post hoc.

Data was also obtained for the following: glycogen (FIG. 11), hemoglobin Alc (HbAlc; FIG. 12), blood urea nitrogen (BUN; FIG. 13), creatinine (FIG. 14), aspartate aminotransferase (AST; FIG. 15), and alanine aminotransferase (ALT; FIG. 16). Here, the 75 mg/kgbw Complex 1 dosage significantly recovered glycogen level to 2.01 mg/g and 2.00 mg/g tissue on day 30 and day 90, respectively. In addition, the 75 mg/kgbw Complex 1 dosage significantly reduced the BUN levels of STZ diabetic mice to 20.11 mg/dl and 20.03 mg/dl in 30-days and 90-days, respectively as well as significantly reducing creatinine levels.

Example 3

In Vivo Effect of Oral Administration of Complex 1

Healthy adult male albino *Rattus norvegicus* Wistar rats weighing 170-200 g were procured from Sri Raghavendra Enterprises, Bangalore, Karnataka, India, acclimatized, and diabetes induced as set forth in Example 2.

Complex 1 was prepared as for Example 2 and administered orally by oral gavage to the STZ-induced diabetic rats. The dose-response of the drug was monitored for a period of 30 and 90 days using drug doses of 100 and 200 mg/kgbw administered once every five days. Spectrophotometric measurements and statistical analysis were obtained as in Example 2.

Figure 17A:
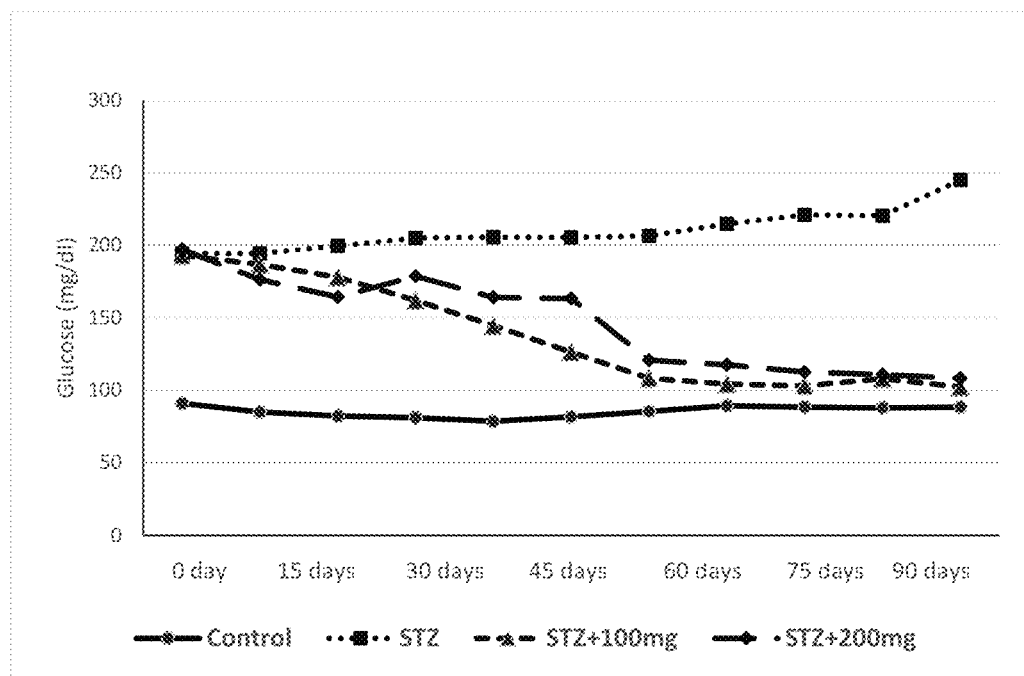
FIGS. 17A-17B: Dose-response of Complex 1 on blood glucose over a period of 30 days and 90 at doses of 100 and 200 mg/kgbw administered orally once every five days to STZ-induced diabetic rats.
Figure 17B:
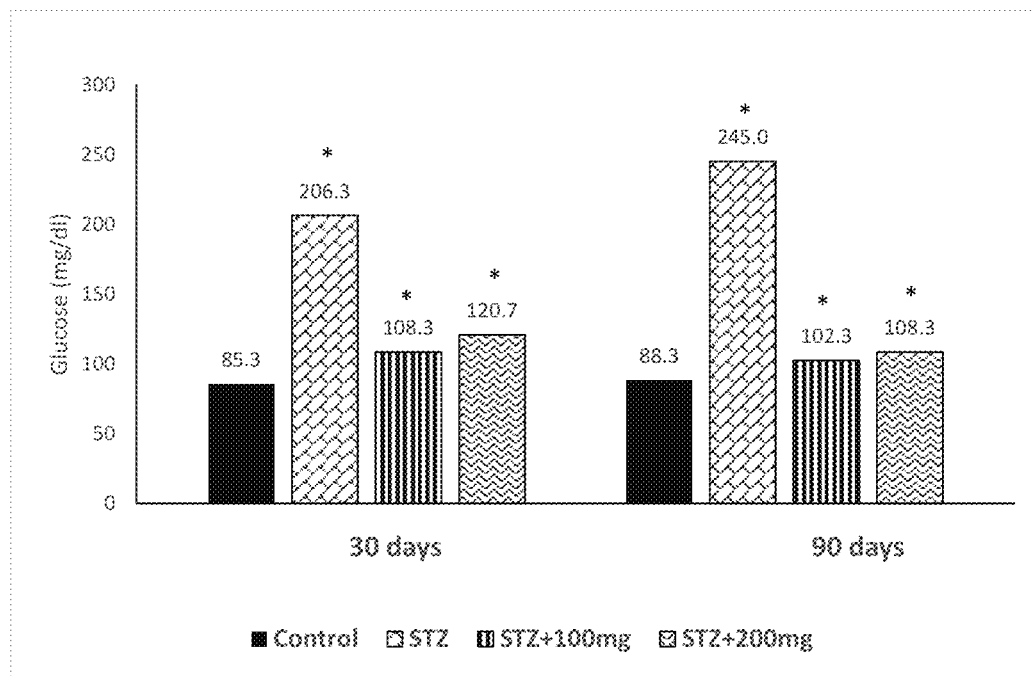
Figure 18:
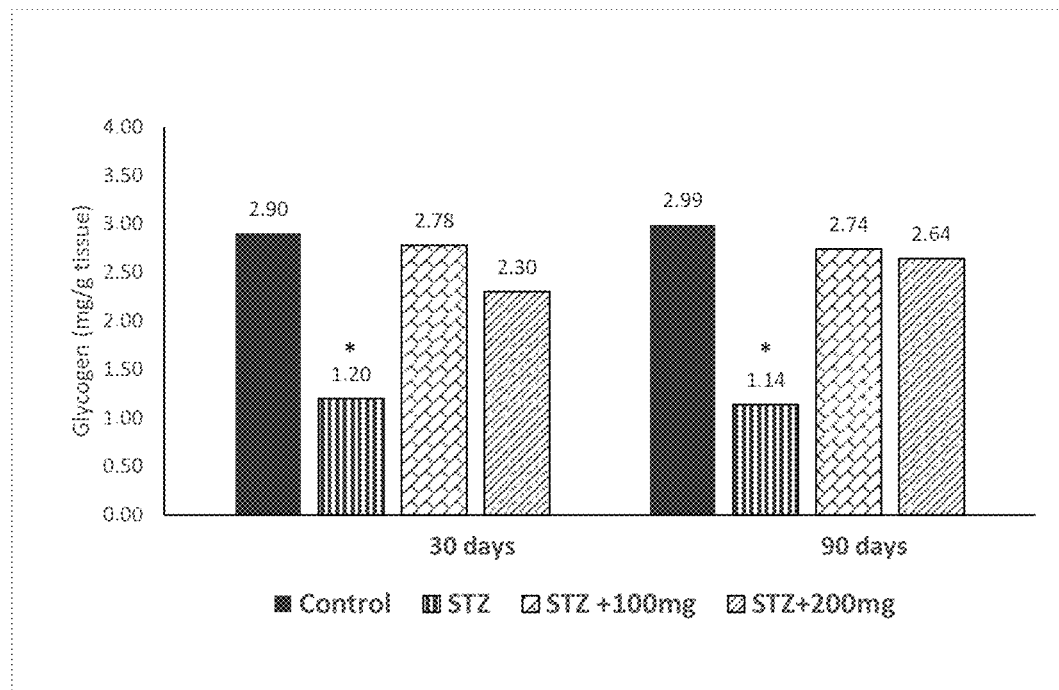
FIG. 18: Glycogen response of Complex 1 over a period of 30 days and 90 at doses of 100 and 200 mg/kgbw administered orally once every five days to STZ-induced diabetic rats. $P<0.05$ analysis via One-way analysis of variance (ANOVA) using Tukey HSD post hoc.
Figure 19:
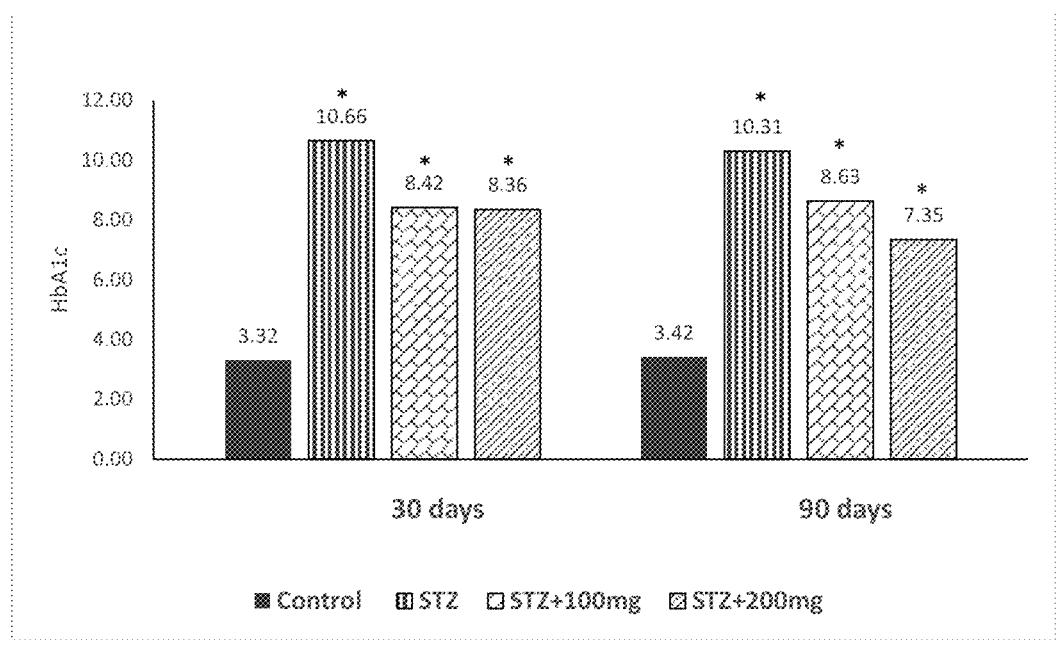
FIG. 19: HbA1c response of Complex 1 over a period of 30 days and 90 at doses of 100 and 200 mg/kgbw administered orally once every five days to STZ-induced diabetic rats. $P<0.05$ analysis via One-way analysis of variance (ANOVA) using Tukey HSD post hoc.
Figure 20:
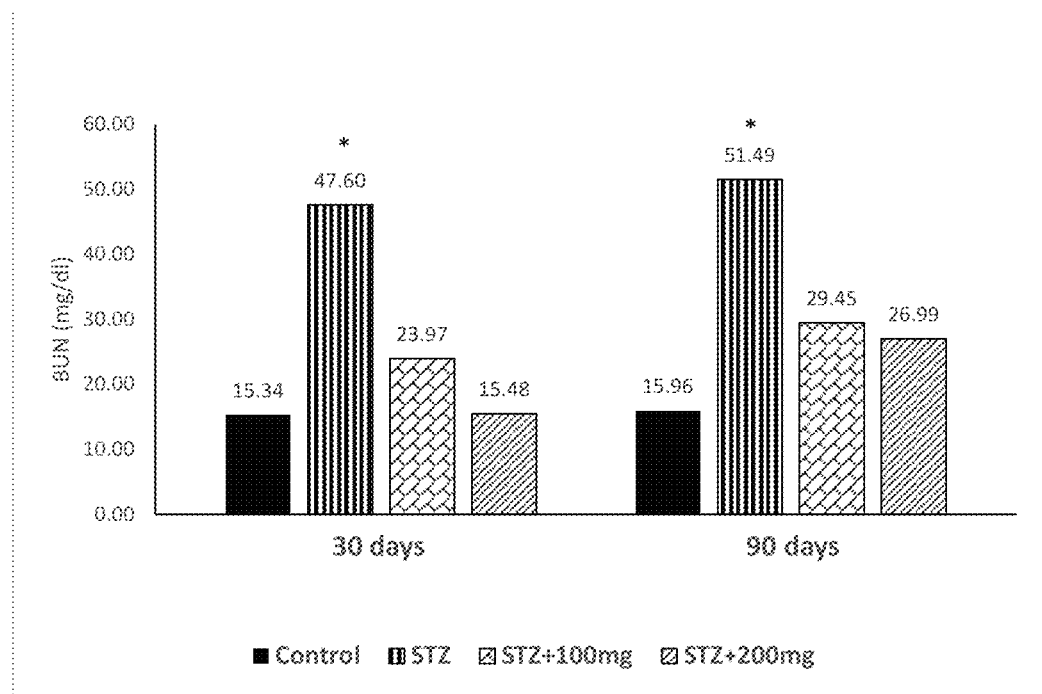
FIG. 20: BUN response of Complex 1 over a period of 30 days and 90 at doses of 100 and 200 mg/kgbw administered orally once every five days to STZ-induced diabetic rats. $P<0.05$ analysis via One-way analysis of variance (ANOVA) using Tukey HSD post hoc.
Figure 21:
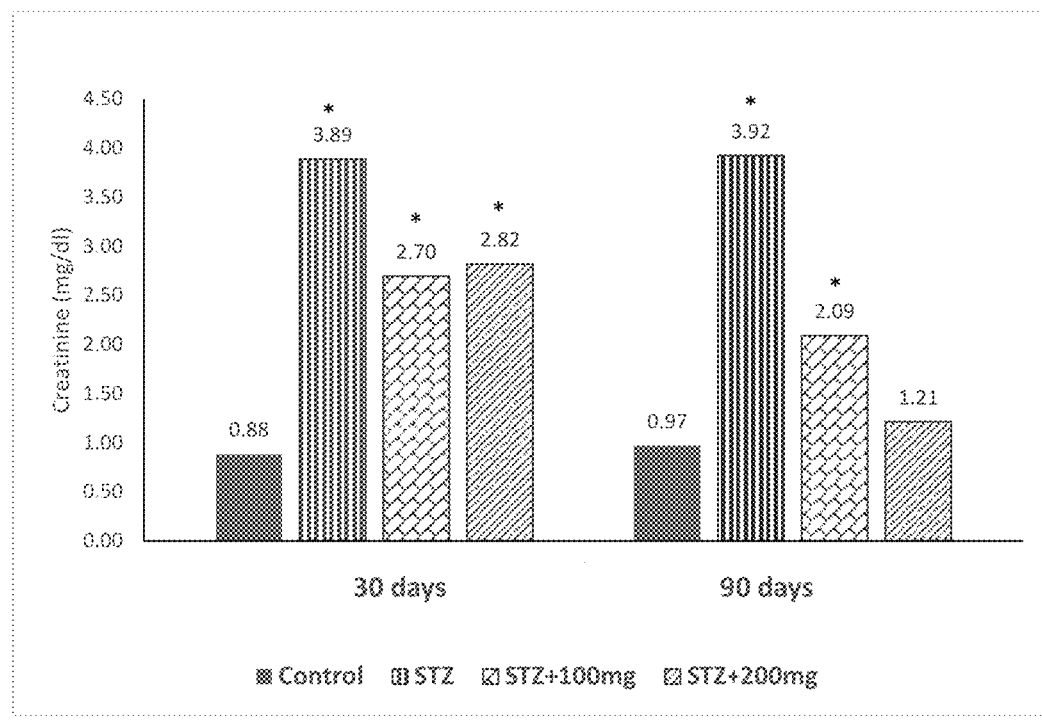
FIG. 21: Creatine response of Complex 1 over a period of 30 days and 90 at doses of 100 and 200 mg/kgbw administered orally once every five days to STZ-induced diabetic rats. $P<0.05$ analysis via One-way analysis of variance (ANOVA) using Tukey HSD post hoc.
Figure 22:
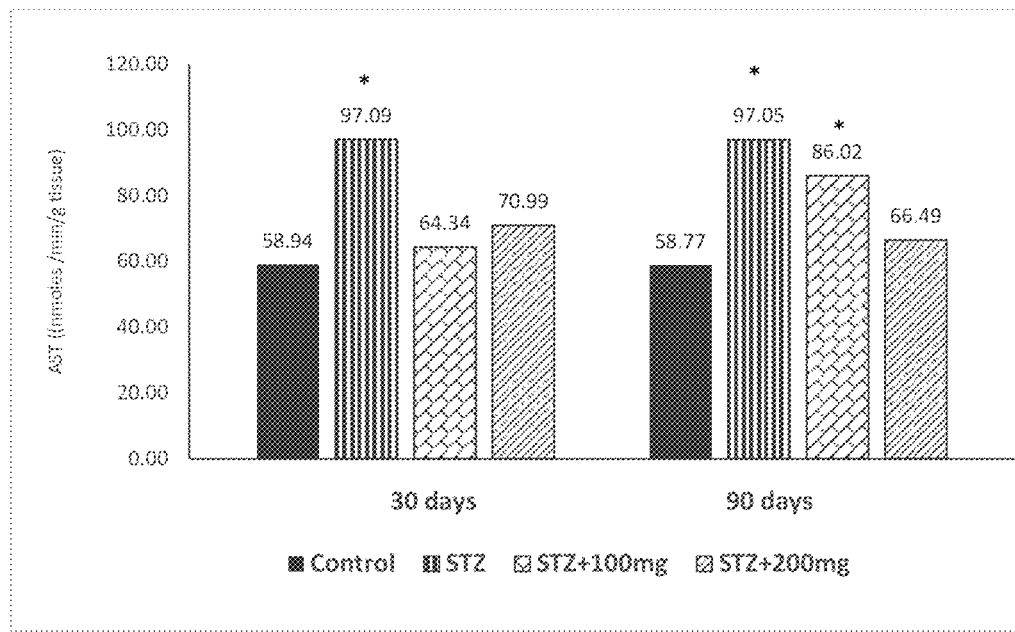
FIG. 22: AST response of Complex 1 over a period of 30 days and 90 at doses of 100 and 200 mg/kgbw administered orally once every five days to STZ-induced diabetic rats. $P<0.05$ analysis via One-way analysis of variance (ANOVA) using Tukey HSD post hoc.
Figure 23:
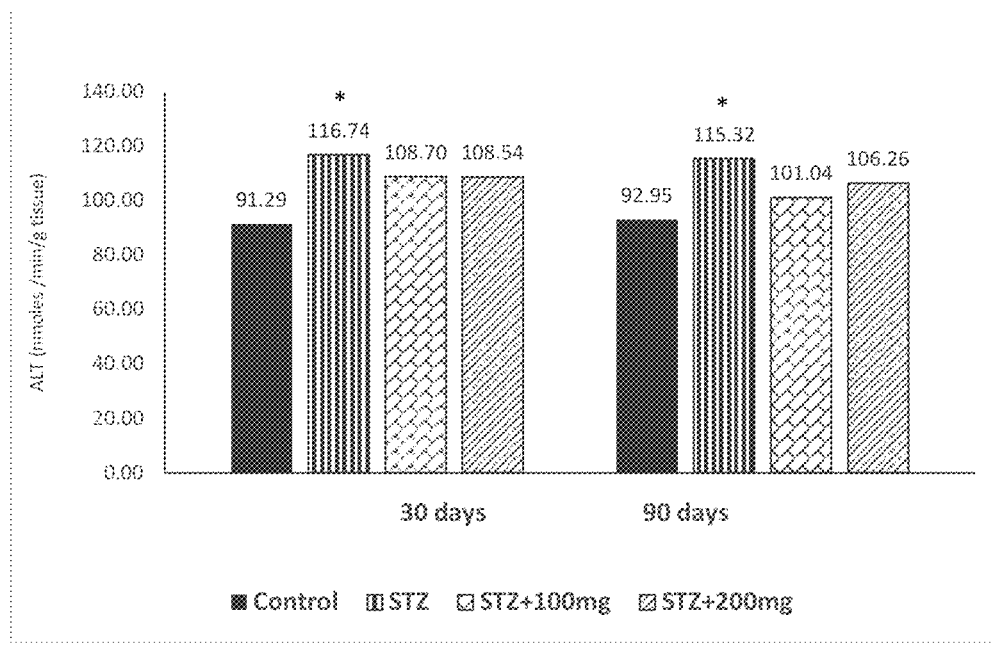
FIG. 23: ALT response of Complex 1 over a period of 30 days and 90 at doses of 100 and 200 mg/kgbw administered orally once every five days to STZ-induced diabetic rats. $P<0.05$ analysis via One-way analysis of variance (ANOVA) using Tukey HSD post hoc.
Figure 25:
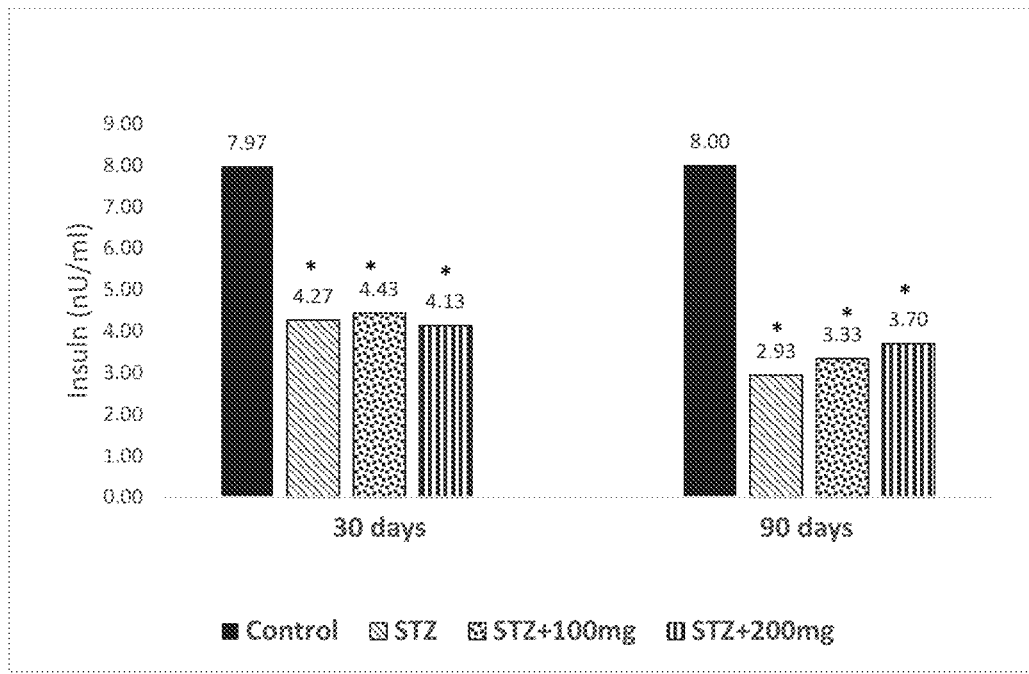
FIG. 25: Insulin response to Complex 1 over a period of 30 days and 90 at doses of 100 and 200 mg/kgbw administered orally once every five days to STZ-induced diabetic rats. $P<0.05$ analysis via One-way analysis of variance (ANOVA) using Tukey HSD post hoc.

Oral administration of Complex 1 on STZ diabetic rats at a dose of 100 mg/kgbw revealed an insignificant (P<0.05) decrease in blood glucose levels to 108 mg/dl and 102 mg/dl on day 30 and 90, respectively (FIGS. 17A-17B), as well as having a significant effect on decreasing BUN levels (FIG. 20) and reducing AST and ALT levels (FIG. 22 and FIG. 23). There was a significant effect on increasing the glycogen levels (FIG. 18) as well as a significant reduction in insulin levels as compared to the control (FIG. 25); however, there was no significant effect on creatinine levels (FIG. 21). In addition, no significant effect was observed for HbA1c levels (7.35 to 8.63 mg %) from that of diabetic rats (10.6 to 10.33 mg %) (FIG. 19).

Example 4

Complex 1 Loaded Chitosan Dextran-Sulfate Hydrogel

A 0.25% Chitosan (CS) solution was prepared by dissolving 0.25 g CS in 100 ml 1.75% Acetic Acid solution. A 1% dextran sulphate (DS) solution was also prepared by dissolving 1.0 g DS in 100 ml 0.5 M NaCl solution. Varying masses of Complex 1 were dissolved in 25 ml DS solution, using sonication and gentle warming (40° C.). 25 ml of CS solution was then added to each of the vanadyl/DS solutions and the evolved suspensions were agitated for 1 hour in darkness.

After the loading period, the samples were acidified to pH 2 by the addition of 100 μl of concentrated HCl to each sample. The acidified suspensions were allowed to shake for a further hour after which they were centrifuged at 10,000-12,000 rpm for 5 minutes. The supernatants were then collected and the hydrogels shaken in 20 ml pH 2 buffer solution (0.41 ml HCl (12.1 M)+50 ml (0.01 M KCl (aq)), after which the hydrogels were again centrifuged at 10,000-12000 rpm for 5 minutes and the wash solution decanted and collected.

Drug Release from Hydrogel at Increasing pH

An orally administered drug encounters a changing pH environment as it passes from the stomach to the small intestine, where maximum absorption is known to take place. The average time of residence in the stomach, which is pH 2, is 4 hours before passing to the small intestine, having a pH of 7.4. To better simulate the in vivo release patterns from the hydrogel (when administered orally), a time and pH dependent drug-release experiment was performed.

For each mass of Complex 1 used, release from the loaded hydrogel was done in triplicate.

The selective release of the drug in an increasing pH environment was demonstrated by adding a 20 ml aliquot of pH 2 buffer to the loaded hydrogel samples and then agitating in darkness for 15 minutes. Samples were then centrifuged at 10,000-12000 rpm for 5 minutes and 100 μl collected for spectral analyses. 100 μl of the pH 2 buffer was used to replace the removed volumes of each sample and the samples were returned for further agitation in darkness for further fixed periods of time (i.e. 45 minutes, 1.5 hours, 3 hours, and 4 hours from the time of commencement of the release procedure).

The absorbance values of the collected aliquots were recorded at 266 nm using a Perkin Elmer Lambda 750 spectrophotometer.

After the 4 hour time period, samples were centrifuged at 10000-12000 rpm for 5 minutes and the supernatants decanted and collected. 20 ml pH 7.4 buffer (80.20 ml (1.74%) $Na_2HPO_4$+19.8 ml 1.361%) $NaH_2PO_4$) was then added to each of the samples and sediments dispersed via agitation for 15 minutes. Samples were centrifuged at 10000-12000 rpm for 5 minutes and 100 μl removed from each for spectral analysis. 100 μl of pH 7.4 buffer was added to each sample to replace the removed volume and samples returned to agitate in the dark. This procedure was repeated at 45 minutes, 1.5 hours, 3 hours, 4 hours, 6 hours, and 12 hours (from the time of addition of the pH 7.4 buffer).

The absorbance values of the collected aliquots were recorded at 266 nm using a Perkin Elmer Lambda 750 spectrophotometer.

Example 5

Preparation of Nanoparticles (MCM (Mobile Cooperation Materials)—41)

1.0 g (2.74 mmol) Hexadecyl trimethylammonium bromide (CTAB) was added to 480 ml deionized (DI) water (500 ml RB flask) and set to stir vigorously at 80° C. 3.5 ml NaOH (2 M) was then added to the resultant mixture and allowed to stir for a further 15 minutes. After the elapsed time, 5 ml (22.4 mmol) Tetraethyl orthosilicate (TEOS) was added drop wise, and the reaction mixture was then left to stir for a further 2 hours at 80° C. The resultant milk white solution was centrifuged (10,000 rpm for 5 minutes) and the resultant residue was washed twice with double distilled, deionized (DI) water and twice with ethanol (EtOH). The CTAB template was removed by refluxing for 6 hours with acidified EtOH (500 μl HCl in 50 ml EtOH). The finally MCM-41 product was then washed twice with DI water and twice with ethanol (EtOH) and left for 24 hours in a Hot Air Oven (80° C.) to dry (yield=1.14 g). The product was characterized by Field Emission Scanning Electron Microscopy (FESEM), Transmission Electron Microscopy (TEM), Nitrogen Sorption Isotherm Studies, Powdered X-Ray Diffraction Technique, and Dynamic Light Scattering (DLS) Studies. Results are shown in FIGS. 3A-3F.

Example 6

Uncoated MCM-41 Drug Loading

Drug loading was accomplished as follows, using non-coated nanoparticles.

Figure 4A:
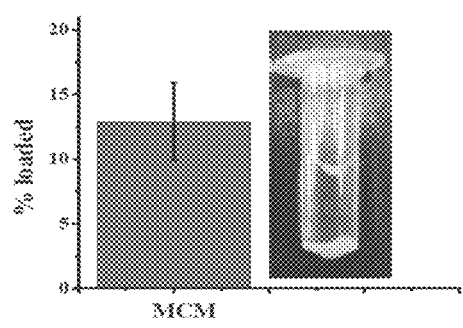
FIGS. 4A-4B.
Figure 4B:
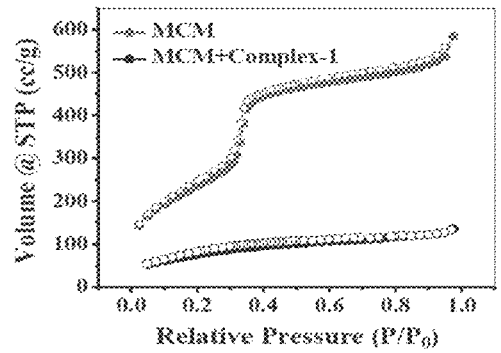

Loading of the drug into the channels of uncoated MCM-41 nanoparticles was done by soaking the nanoparticles in 10 ml of a 10 mM solution (1 ml drug solution:5 mg MCM-41) of Complex 1 in pH 7.4 buffer solution for 24 hours, with gentle agitation. Percentage loading was then calculated through the application of Beer Lambert's equation to the UV-Vis measurement data of the loading solution. The calculated concentration difference, which corresponded to the supernatant absorbance of the nanoparticle pre-loaded vs. nanoparticle post-loaded, gave a reliable estimate of the quantity of drug residing in the carrier (FIG. 4A). Further, BET adsorption/desorption comparisons of the loaded to unloaded nanoparticle's confirmed maximum occupancy in the MCM channels (FIG. 4B).

Example 7

Uncoated MCM-41 Complex 1 Drug Release In Vitro

Complex 1 drug release studies were conducted over a 24 hour period with Complex 1 release rate being monitored via UV-Vis spectrophotometry at 266 nm ($\pi$-$\pi$* transitions of the ligand). Initial release data revealed a high rate of release at the low pH's which was attributed to the characteristic pKa value of the surface silanol groups of the MCM-41 nanoparticle (FIG. 5).

Figure 5:
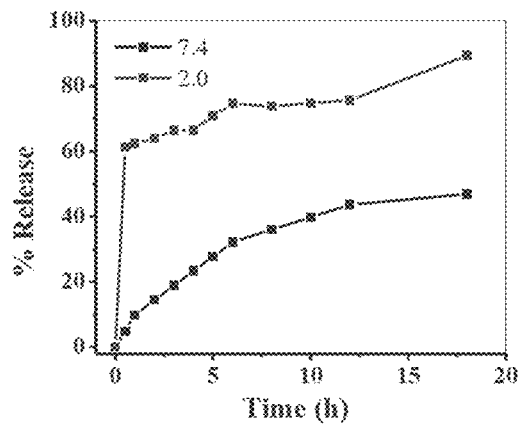
FIG. 5 and FIG. 6: Graphical comparison highlighting the rate of release of the drug Complex 1 in pH 2 relative to that of pH 7.4.

In contrast, at pH 7.4, a relatively consistent and steady release was observed, which was found to be a desirable characteristic of a carrying agent; a sustained release would avoid a high concentration drug "dump" which could possibly lead to a lethal or toxic dose delivery (FIG. 5).

Example 8

Nanoparticle Coating for Drug Release in the Intestine

To provide the needed protective barrier to the nanoparticles, 10 mg of MCM-41 nanoparticles were suspended in 1 ml DI water and sonicated until visually fully dispersed. 1.0 ml of 1% DS solution (100 mg DS per 10 ml (0.5 M) NaCl solution) was then added to the 1 ml MCM-41 dispersion and sonicated for 30 minutes.

After sonication, the solution was centrifuged for 5 minutes at 12000 rpm and the supernatant removed. The sedimented nanoparticles were washed by re-dispersing the sample in 1 ml double distilled water via sonication and centrifuging the resulting suspension for 5 minutes at 12000 rpm.

1.0 ml of a 0.25% CS solution (25 mg per 10 ml (1.75%) acetic acid) was added to the DS-layered nanoparticles and sonicated for 30 minutes. The washing procedure (as described in paragraph [184]) was conducted for this layer as well to furnish a nanoparticle with a single DS-CS hydrogel coating.

Figure 8A:
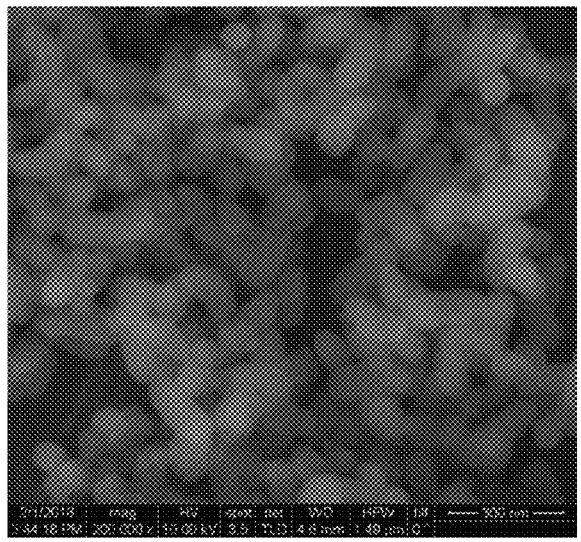
FIGS. 8A-8B.
Figure 8B:
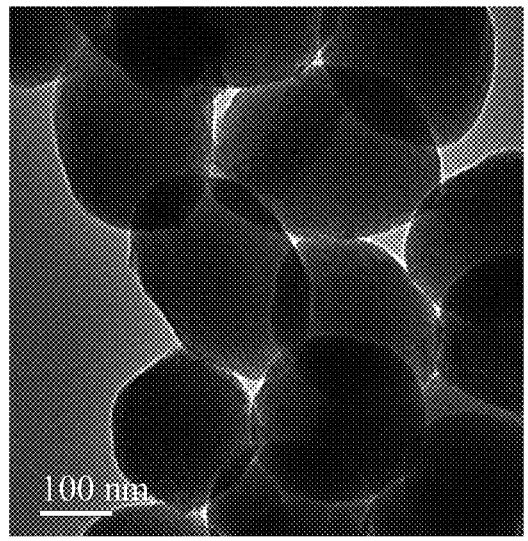
Figure 9:
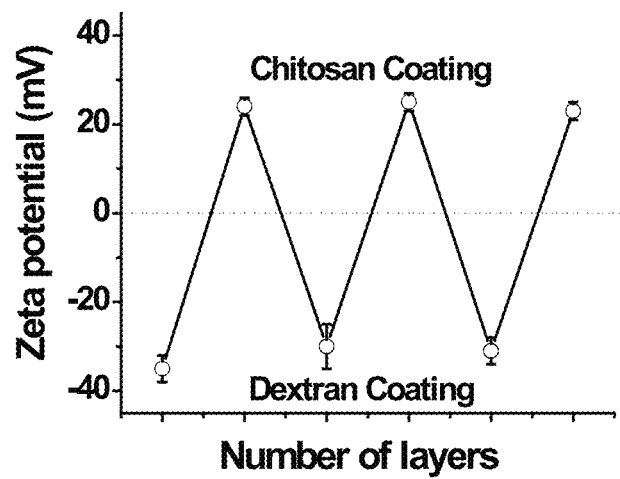
FIG. 9: Zeta potential measurements in relation to the layer-by-layer coatings of the MCM-41 nanoparticles.

Additional layers of the DS-CS coating were achieved by repeating the above described process to furnish a total of six (6) layers; three layers of DS and three layers of CS. Analyses using Scanning Electron Microscopy (SEM) and Transmission Electron Microscopy (TEM) was done and compared to the SEM and TEM images for uncoated MCM-41 particles (see FIGS. 3A-3B). Although there were no discernable differences between the uncoated to the coated nanoparticles from the SEM images (FIG. 8A), it was evident from the TEM image that the hydrogel layer was present on the coated nanoparticles due to the obscureness of the MCM-41 channels (see FIG. 8B). The layer by layer coating was further confirmed using zeta potential measurements (FIG. 9) using a ZETASIZER® MALVERN® Instrument.

Example 9

Coated MCM-41 Drug Loading 20 ml of a 6.91 mM solution of Vanadyl Complex 1 was prepared by dissolving 0.040 g Complex 1 in 20 ml 0.01 M pH 7.4 buffer. Approximately 2 ml of the Complex 1 solution was then added to each sample vial containing the coated nanoparticles in a 1 ml: 50 mg ratio (see Table 3).

TABLE 3

Stoichiometric Ratios Used for Drug Release in Fixed pH

| Sample | Coating Layers | Mass of MCM-41 (mg) | Volume of Complex 1 (ml) |
|---|---|---|---|
| 1 | Triple | 10.3 | 2.06 |
| 2 | Triple | 10.6 | 2.12 |
| 3 | Triple | 10.3 | 2.06 |
| 4 | Triple | 10.1 | 2.02 |
| 5 | Triple | 10.1 | 2.02 |
| 6 | Triple | 10.3 | 2.06 |

The coated nanoparticles were left to soak (load) in solution with Complex 1 at pH 7.4 in the dark with constant agitation for 18-24 hours. After the loading period, samples 1-3 were acidified to pH 2 by the addition of 100 μl of concentrated HCl to each sample. The acidified suspensions were allowed to shake for a further hour, after which they were centrifuged at 10-12,000 rpm for 5 minutes.

Example 10

Drug Release from Coated MCM-41 at Fixed pH

Following centrifugation, the supernatant was decanted and samples 1-3 washed using pH 2.0 buffer. Samples 4-6 were washed with pH 7.4 buffer. The tubes were again centrifuged at 10-12,000 rpm for 5 minutes and their respective supernatants collected.

The selective release of the drug in a fixed pH environment was initiated by adding another 2 ml aliquot of pH 2.0 buffer (previously described) to samples 1-3, while samples 4-6 received another 2 ml aliquot of pH 7.4 buffer. Samples were then agitated in darkness for 15 minutes. Samples were then centrifuged at 10-12000 rpm for 5 minutes and 100 μl collected for spectral analyses. 100 μl of the respective buffers was used to replace the removed volumes of each sample and samples returned for further agitation in darkness for further fixed periods of time (i.e. 45 minutes, 1.5 hours, 3 hours, and 6 hours from the time of commencement of the release procedure). The absorbance values of the samples were recorded at 266 nm using a Perkin Elmer Lambda 750 spectrophotometer.

Two calibration curves were generated to aid in the determination of the relative concentrations of drug released from the loaded nanoparticles. Serial dilutions of a 4.05 mM solution of Complex 1 in 0.01 M pH 2 buffer and a 3.68 mM solution of Complex 1 in 0.01 M pH 7.4 buffer were prepared and the respective absorbance values recorded as follows:

TABLE 4

Absorbance values for Standard Solutions of Complex 1

| Molarities of standards in pH 2 buffer (mM) | Molarities of standards in pH 7.4 buffer (mM) |
|---|---|
| 4.05 | 3.68 |
| 2.03 | 1.84 |
| 1.01 | 0.92 |
| 0.51 | 0.46 |
| 0.26 | 0.23 |

Figure 6:
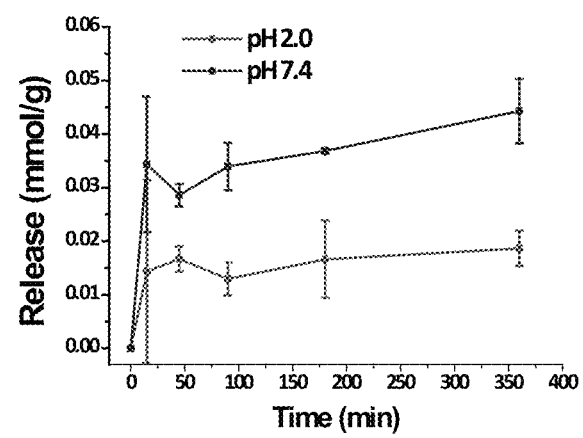

Results showing the selective release rates of Complex 1 are illustrated in FIG. 6.

Example 11

Drug Release from Coated MCM-41 at Increasing pH

A triple layered hydrogel coating of the MCM-41 nanoparticles and Complex 1 was generated as described above resulting in the following stoichiometric ratios (Table 5):

TABLE 5

Stoichiometric Ratios Used for Drug Release in Increasing pH

| Sample | Coating Layers | Mass of MCM-41 (mg) | Volume of Complex 2 (ml) |
|---|---|---|---|
| 7 | Triple | 10.7 | 2.14 |
| 8 | Triple | 10.8 | 2.16 |
| 9 | Triple | 10.3 | 2.06 |

For MCM-41 samples 7-9, Complex 1 was loaded and acidified as described above (Paragraph [187]), however a ratio of 1 ml of drug solution:5 mg of MCM-41 was used.

A 100 µl aliquot was taken from each sample for spectral analysis, at 5 minutes from the time of commencement of the release procedure; and 100 µl of the pH 2 buffer was used to replace the removed volume of each sample and the samples were returned for further agitation in darkness. More aliquot samples were taken for further fixed periods of time (i.e. 45 minutes, 1.5 hours, 3 hours, and 4 hours).

The absorbance values of the collected aliquots were recorded at 266 nm using a Perkin Elmer Lambda 750 spectrophotometer.

After the 4 hour time period, samples were centrifuged at 10000-12000 rpm for 5 minutes and the supernatants decanted and collected. 2 ml pH 7.4 buffer was then added to each of the samples and sediments dispersed via agitation for 15 minutes. Samples were centrifuged at 10000-12000 rpm for 5 minutes and 100 µl removed from each for spectral analysis. 100 µl of pH 7.4 buffer was added to each sample to replace the removed volume and samples returned to agitate in the dark. This procedure was repeated at 45 minutes, 1.5 hours, 3 hours, 4 hours, 6 hours, and 12 hours (from the time of addition of the pH 7.4 buffer).

Figure 7:
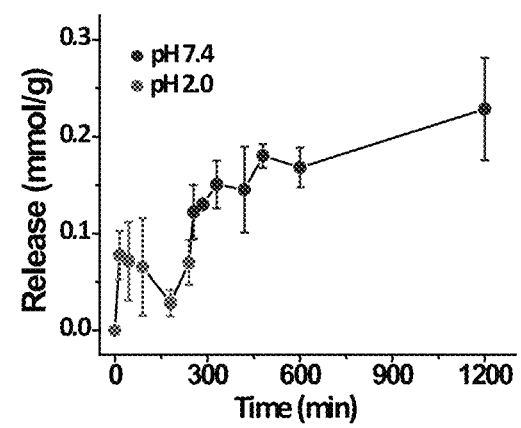
FIG. 7: Percentage release vs time plot at varying pH, highlighting the high rate of release at pH 7.4, relative to that at pH 2.

The absorbance values of the collected aliquots were recorded at 266 nm using a Perkin Elmer Lambda 750 spectrophotometer. Results are shown in FIG. 7.

We claim:

1. A compound according to Formula 1:

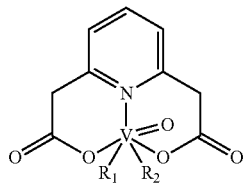

Formula 1 wherein:
R$_1$ and R$_2$ are independently (C$_1$-C$_{18}$) alkyl, —NH$_2$—COH—CHOH, —NH$_2$—(C$_1$-C$_{18}$)alkyl, NH$_2$—(C$_1$-C$_{18}$)alkyl-NH$_2$, =O, aryl or dihydroxy-substituted aryl, or a monodentate ligand, wherein each monodentate ligand is halo or OH$_2$;

or a pharmaceutically acceptable salt thereof.

2. The compound according to claim 1, that is Complex I

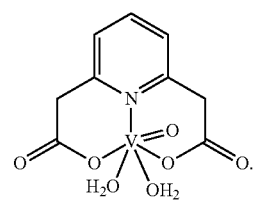

Complex 1

3. A compound according to Formula 2:

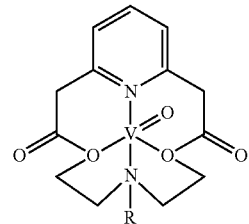

Formula 2 wherein:
R is H, (C$_1$-C$_{18}$)alkyl, aryl or dihydroxy-substituted aryl; or a pharmaceutically acceptable salt thereof.

4. A compound according to Formula 3

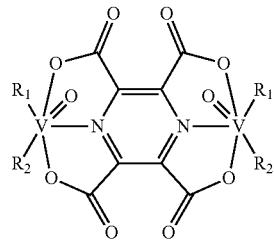

Formula 3 wherein:
R$_1$ and R$_2$ are independently selected from H$_2$O, (C$_1$-C$_8$) alkyl, aryl or dihydroxy-substituted aryl;
or a pharmaceutically acceptable salt thereof.

5. A composition comprising a crystal of the compound according to claim 1.

6. A composition comprising a crystal of the compound according to claim 2.

7. A composition comprising a crystal selected from the group consisting of

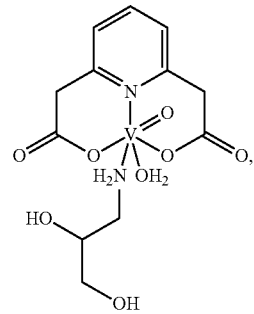

Complex 2

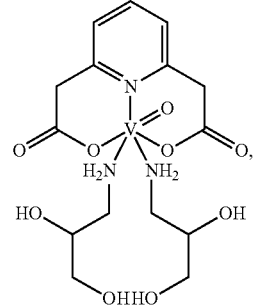

Complex 3

Complex 4
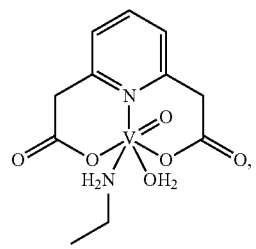
Complex 5
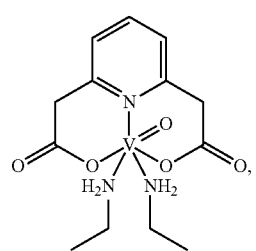
Complex 6
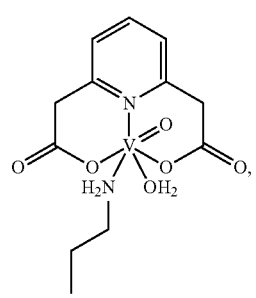
Complex 7
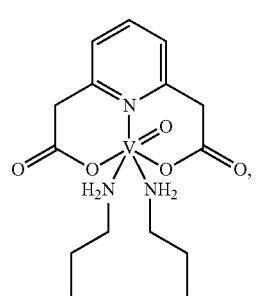
Complex 8
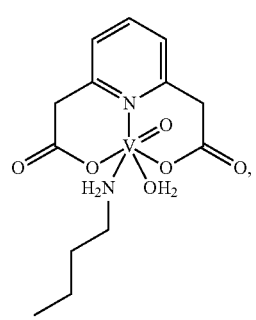
Complex 9
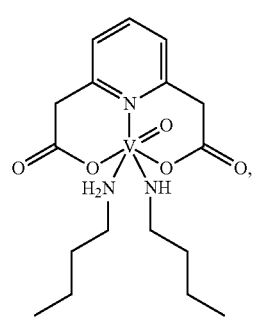
Complex 10
Complex 11
Complex 12
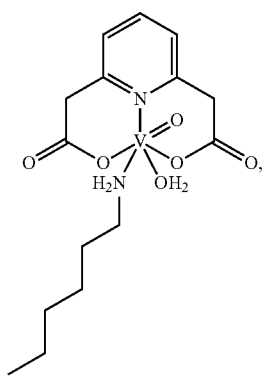

Complex 13
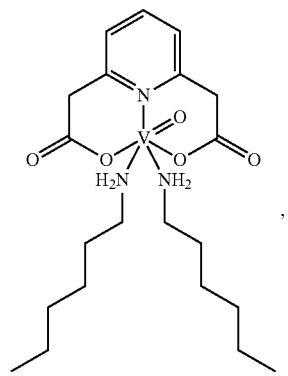
Complex 14
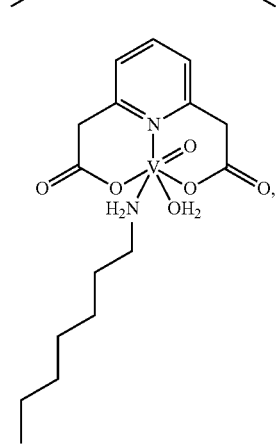
Complex 15
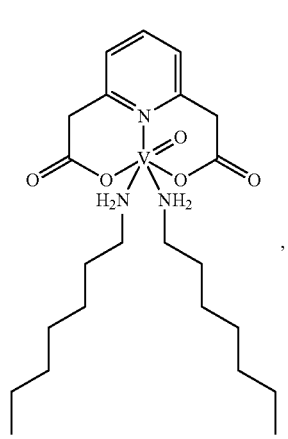
Complex 16
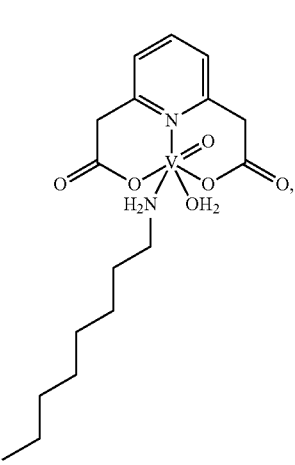
Complex 17
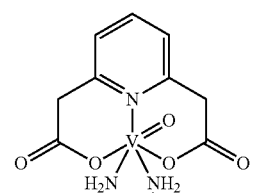
Complex 18
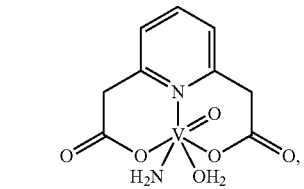
Complex 19
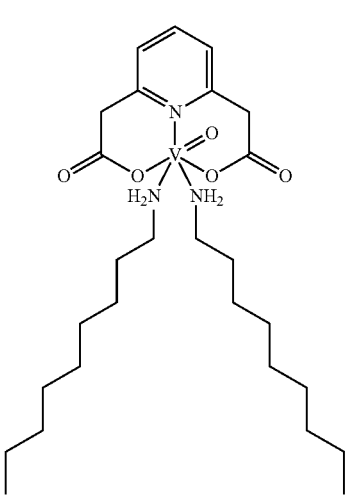

Complex 20
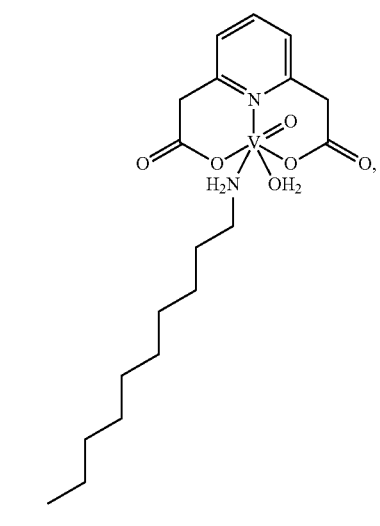
Complex 21
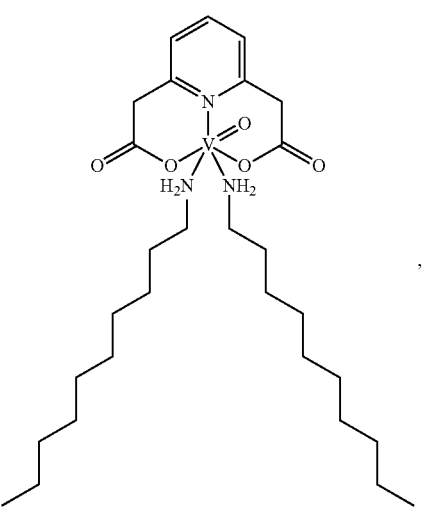
Complex 22
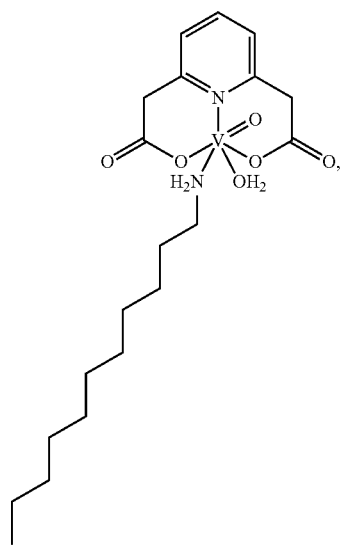
Complex 23
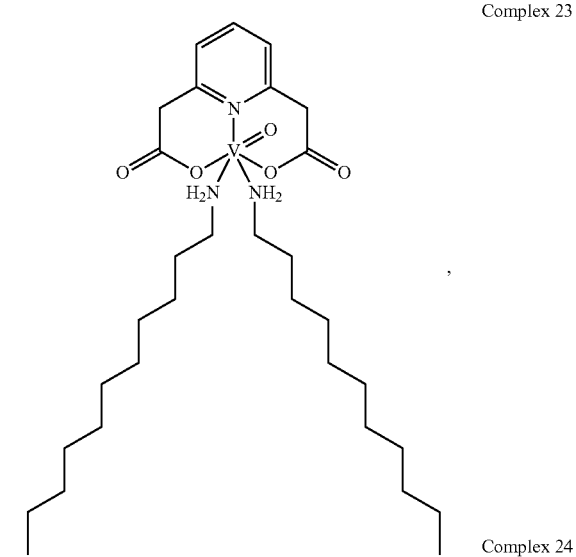
Complex 24
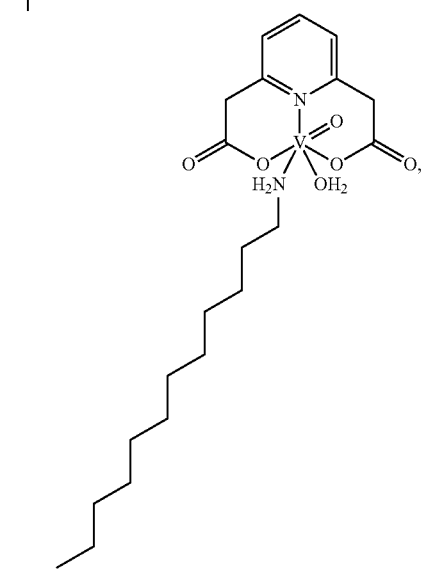
Complex 25

Complex 26

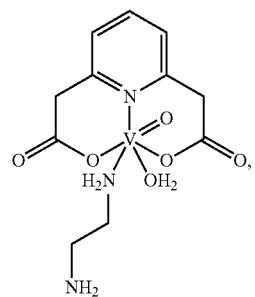

Complex 27

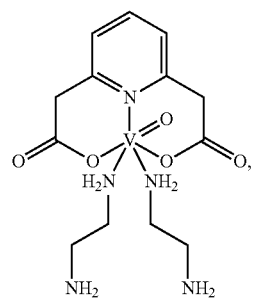

Complex 28

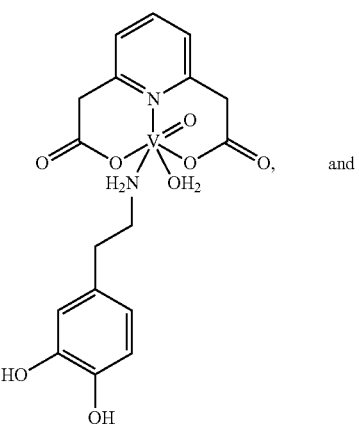 and

Complex 29

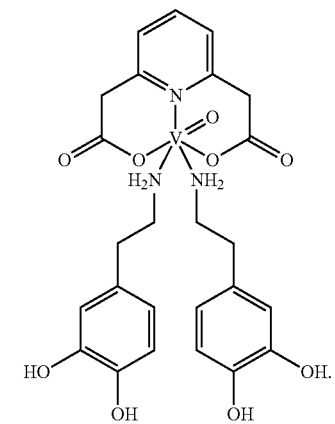

8. The composition of claim 5, wherein the crystal effectively diffracts X-rays and permits the determination of the atomic coordinates of the compound to a resolution of 2.0 Å.

9. A pharmaceutical composition comprising at least one compound according to claim 1, or a pharmaceutically acceptable salt thereof, in association with a pharmaceutically acceptable adjuvant or carrier.

10. The pharmaceutical composition according to claim 9, further comprising at least one additional therapeutic agent(s) selected from the group consisting of a sulfonylurea agent, biguanide agent, alpha-glycosidase inhibitor, thiazolidinedione agent, meglitinide agent, and dipeptidyl-peptidase IV (DPP-4) inhibitor.

11. The pharmaceutical composition according to claim 9, or a pharmaceutically acceptable salt thereof, in association with a nanoparticle carrier.

12. The pharmaceutical composition of claim 11, wherein the nanoparticle carrier is a carbon sphere nanoparticle or a mesoporous silica nanoparticle.

13. The pharmaceutical composition of claim 12, wherein the mesoporous silica nanoparticle is MCM-41.

14. The pharmaceutical composition of claim 11, wherein the nanoparticle is coated with at least one layer of dextran and at least one layer of chitosan or wherein the nanoparticle is coated with at least two alternating layers of dextran and chitosan.

15. A method of treating diabetes mellitus comprising administering to a subject in need thereof an effective amount of at least one compound according to claim 1.

16. The method of treating of diabetes mellitus according to claim 15, wherein the at least one compound is administered orally.

17. The method of treating of diabetes mellitus according to claim 15, wherein the at least one compound is administered once every five days.

18. The method of treating diabetes mellitus according to claim 15, wherein the at least one compound is administered at 50-150 mg/kg of body weight.

19. A method of isolating the crystal of claim 5 comprising a. synthesizing 2,6-pyridinediacetic acid;

b. complexing 2,6-pyridinediacetic acid with vanadyl sulfate;

c. purifying the complex via gel permeation chromatography; and d. crystallizing the purified complex.

* * * * *